(12) United States Patent
Hurst et al.

(10) Patent No.: US 11,311,186 B2
(45) Date of Patent: Apr. 26, 2022

(54) SYSTEM AND METHOD FOR CLEANING A CANNULA DURING A SURGICAL PROCEDURE USING A HINGED TIP

(71) Applicants: Ronald Hurst, Los Angeles, CA (US); Dan Garr, Los Angeles, CA (US)

(72) Inventors: Ronald Hurst, Los Angeles, CA (US); Dan Garr, Los Angeles, CA (US)

(*) Notice: Subject to any disclaimer, the term of this patent is extended or adjusted under 35 U.S.C. 154(b) by 30 days.

(21) Appl. No.: 16/819,633

(22) Filed: Mar. 16, 2020

(65) Prior Publication Data
US 2020/0214549 A1    Jul. 9, 2020

Related U.S. Application Data

(63) Continuation of application No. 13/887,324, filed on May 5, 2013, now Pat. No. 10,595,719, which is a continuation-in-part of application No. 13/784,364, filed on Mar. 4, 2013, now abandoned.

(60) Provisional application No. 61/742,011, filed on Aug. 1, 2012.

(51) Int. Cl.
*A61B 1/12* (2006.01)

(52) U.S. Cl.
CPC .................................. *A61B 1/126* (2013.01)

(58) Field of Classification Search
None
See application file for complete search history.

(56) References Cited

U.S. PATENT DOCUMENTS

| | | | | |
|---|---|---|---|---|
| 5,392,766 A | * | 2/1995 | Masterson | A61B 1/0008 15/244.1 |
| 5,916,145 A | * | 6/1999 | Chu | A61B 1/00071 600/121 |
| 2009/0270686 A1 | * | 10/2009 | Duke | A61B 1/127 600/203 |

* cited by examiner

*Primary Examiner* — Eric W Golightly
(74) *Attorney, Agent, or Firm* — Kim IP Law Group LLC

(57) ABSTRACT

An improved apparatus for cleaning a scope during a surgical procedure using a hinged tip. A scope cleaning apparatus can include a tube configured to be slidably received by a cannula, a hinged tip connected to the tube, and a lens-cleaning portion. The tube can include a proximal portion and a distal portion. Furthermore, the tube, across the proximal portion and the distal portion together can include an outer surface, an inner surface, and a lumen. The inner surface can be configured to slidably receive a viewing scope. The lumen can be defined by the inner surface. The lens-cleaning portion can be coupled to the hinged tip and can be configured to engage at least a portion of the viewing scope.

18 Claims, 19 Drawing Sheets

SYSTEM AND METHOD FOR CLEANING A CANNULA DURING A SURGICAL PROCEDURE USING A HINGED TIP

CROSS-REFERENCE TO RELATED APPLICATIONS

This application is a continuation of U.S. application Ser. No. 13/887,324 filed May 5, 2013, issuing on Mar. 24, 2020 as U.S. Pat. No. 10,595,719 and entitled System and Method for Cleaning a Cannula During a Surgical Procedure using a Hinged Tip, which is a continuation-in-part of U.S. application Ser. No. 13/784,364 filed Mar. 4, 2013, entitled Improved System and Method for Cleaning a Cannula during a Surgical Procedure, and claims priority to U.S. Provisional Application No. 61/742,011 filed Aug. 1, 2012, entitled Cannula and Scope Cleaning Apparatus and Associated Methods of Use, the contents of all of which are incorporated herein by reference in their entirety for all purposes.

BACKGROUND

The present disclosure generally relates to the field of surgery. In particular, the disclosure relates to instrumentation utilized during invasive procedures. More particularly, disclosed herein are apparatus and associated methods of use that provide cleaning of a cannula (or other access device), as well as cleaning for a viewing scope (e.g. laparoscope and other viewing scopes) for example, during particular invasive surgical procedures.

Minimally invasive surgical (MIS) procedures, which typically utilize viewing scopes, provide various advantages over open surgical procedures. In an open surgical procedure, a patient's skin and tissues are cut such that operating personnel are granted direct access to patient structures or organs. Such cuts and openings are necessarily of significant size in order for the structures and tissues involved to be seen and readily accessible. Accordingly and undesirably, patient structures or organs are thus directly exposed to the air of the operating room (which increases the exposure of the patient's structures or organs to possible contaminants) and results in large incisions that require longer recovery times as compared to MIS procedures. MIS procedures, on the other hand, typically provide the patient with several advantages including reduced blood loss, reduced post-operative patient discomfort, shortened recovery and hospitalization time, smaller incisions (e.g. minimized scarring) and reduced exposure of internal organs to possible contaminants.

As mentioned above, MIS procedures generally utilize viewing scopes, such as laparoscopes permitting remote visualization of a surgical site within a patient's body as the surgical procedure is being performed. For example and during a laparoscopic procedure, the patient's abdominal or pelvic cavity is accessed through two or more relatively small incisions rather than through a single large incision that is typically utilized during conventional surgery. Exemplary procedures which may be performed laparoscopically include, but are not limited to, cholecystectomy, hysterectomy, gastrectomy, appendectomy, bowel resection, herniorrhaphy, ovarian cystectomy and the like.

Viewing scopes, such as laparoscopes, usually consist in part of a rigid rod or shaft having a lens at one end (a distal end) and an eyepiece and/or integrated visual display at the other. The viewing scope may also be connected to a remote visual display device or a video camera to record the surgical procedure.

As previously mentioned, during laparoscopic surgery one or more small incisions are formed in the abdomen, and a trocar within a cannula is inserted through the incision to form a pathway providing access to an abdominal cavity, for example. The trocar, which by insertion into the patient is typically then soiled by bodily tissue and/or fluid, is subsequently withdrawn from the abdominal cavity and within the cannula, leaving behind bodily tissue and/or fluid on the inside surface of the cannula. If the cannula is to be utilized in conjunction with a viewing scope, it is found that upon insertion of a viewing scope therethrough, the viewing scope becomes soiled and in particular a lens portion (portion of the viewing scope which picks up the operative field) becomes obstructed, interfering with and obstructing a clear view of the internal operative field.

During a typical MIS procedure, viewing scopes are inserted and removed through a cannula multiple times, during which time operations at the surgical site and/or each insertion and each removal the viewing scope encounters blood, bodily fluids, pieces of tissue, fat or other bodily material that can adhere to the scope's lens portion and fully or partially impede visibility. Furthermore and much like the withdrawal of the trocar upon initial insertion of the cannula, a viewing scope can draw fluid from inside a patient's body into the cannula, where the fluid is deposited and can be picked up by the viewing scope when reinserted into the cannula. As a result, visualization through the viewing scope can be significantly diminished. Minimization or elimination of repetitive withdrawal and insertion of the viewing scope from the patient through the cannula is desirous, however, the viewing scope's lens requires cleaning to restore visibility, often several times during a single surgical procedure. Typically, the only solution to fogging/condensation and debris collection on the lens is removal of the viewing scope from the body cavity and defogging or cleaning the lens by wiping it with a cloth, warming the scope tip, or utilizing another defogging method such as provided by Dexide, Fort Worth, Tex., which sells a fog reduction/elimination device (FRED.sup®) which comprises a sponge and a bottle of cleaning solution, whereby a viewing scope is removed from the patient to permit cleaning by wiping the lens portion onto the sponge. It has also been proposed to incorporate a spray wash nozzle on the viewing scope itself and/or in conjunction with introducing a flow of gas across a lens portion in order to permit cleaning of a lens portion without removing the scope from the patient. While addressing the needs of efficiency, the requirement of incorporating a washing system in the viewing scope itself does not permit cleaning of existing viewing scopes that are already in use. Such viewing scopes can be relatively expensive, limiting the ability to replace such scopes with models incorporating a wash system. Other methods and apparatus for cleaning a scope lens are disclosed in U.S. Pat. No. 5,375,589 filed Oct. 18, 1993; U.S. Pat. No. 5,392,766 filed Oct. 6, 1993 and U.S. Patent Application Publication Pub. No. US 2006/0293559, filed Jun. 24, 2005, all herein incorporated by reference in their entirety.

The need to remove the viewing scope to defog and remove debris from the lens portion is an inconvenience that interrupts and undesirably prolongs surgical procedures, increasing the chances of complications and contamination through repeated viewing scope insertion and removal.

Therefore it would be desirable to provide alternative apparatus and methods for cleaning surgical viewing scopes in situ, i.e., without the need to remove the viewing scope from the patient, as well as an apparatus that cleans and maintains the cleanliness of a cannula utilized in conjunction with the viewing scope. Such apparatus and methods should preferably require minimum or no modification of the viewing scope and preferably require minimum or no modification of other instruments used in performing the surgical procedure, e.g., cannulas used for introducing the viewing scope into a subject. Such apparatus and methods can be very effective in removing contaminating debris and fogging of the distal lens of the viewing scope as well as clearing and maintaining cleanliness of the cannula, should be convenient to use, and be low-cost to implement. Some or all of these objectives will be met by the various embodiments described hereinafter.

SUMMARY

Many modern surgical procedures, such as, for example laparoscopic, arthroscopic and thoracoscopic surgeries, utilize a viewing scope in order to view and operate on a subject. The present disclosure generally provides apparatus and associated methods of use for maintaining visibility during such exemplary surgical procedures. Accordingly and in one aspect, a cannula and scope cleaning apparatus is provided that comprises a tube having an inner surface configured to slidably receive a viewing scope and an outer surface having at least a portion of which is absorbent, where the tube is sized and configured to be slidably received by a cannula. The tube has a proximal portion, a distal portion and a lumen therethrough where the wall of the lumen can be absorbent, as well as a lens-cleaning portion coupled to the tube, where the lens-cleaning portion is configured to engage at least a portion of the viewing scope. The proximal portion in all embodiments includes a proximal access port, through which the viewing scope is introduced into the apparatus.

In one embodiment, the cannula and apparatus can further comprise a luminal scaffold extending along at least a portion of the lumen. In particular configurations the lens-cleaning portion is disposed at or near the distal portion of the tube. One or more lens-cleaning portions can be provided in the tube according to particular configurations. The lens-cleaning portion of the apparatus can be made of a resilient material, such as, but not limited to, an elastomeric material, foam, such as an absorbent foam material or the like.

In still another exemplary embodiment, the cannula and scope cleaning apparatus can further include a collar disposed along its length and can be located, in one example, at the proximal portion of the cannula and scope cleaning apparatus. In particular embodiments, the luminal scaffold of the cannula and scope cleaning apparatus can have particular properties, such as, in specific embodiments, being radially deformable or being substantially non-radially deformable, dependent upon the particular configuration desired. In particular embodiments, the luminal scaffold can be comprised of absorbent filaments, as discussed below.

In particular embodiments, a lens-cleaning portion can have an outer diameter that is less than the outer diameter of the tube of an exemplary cannula and scope cleaning apparatus. In still other configurations, the cannula and scope cleaning apparatus can have a lens-cleaning portion having an outer diameter that is substantially equal to the diameter of the tube. The lens-cleaning portion can include an opening, such as an annular or slit opening, for example, through which the viewing scope passes to be introduced into an internal location of a subject, and through which the viewing scope is retracted and engages the lens-cleaning portion for cleaning/wiping.

In further exemplary embodiments, the luminal scaffold of cannula and scope cleaning apparatus can be provided to substantially extend along the length of the lumen that extends therethrough. In particular embodiments, the tube includes an absorbent material along its entire length although it is contemplated that in particular configurations the absorbent material can be provided such that it is not provided continuously along the length of the tube. The absorbent material, as disclosed herein, can be compressible. In other aspects, the tube can have an outer tube diameter greater than an inner diameter of a cannula such that it can provide for a good friction fit within cannulas of differing internal diameters.

Additionally provided herein are exemplary embodiments of a cannula and scope cleaning apparatus for use with a cannula and viewing scope, where the apparatus comprises a multilayered tube having a lumen configured to slidably receive a viewing scope, the multilayered tube including an absorbent layer and a luminal scaffold layer and a lens-cleaning portion coupled to the multilayered tube, where the apparatus configured such that, when the multilayered tube is inserted into a cannula, the absorbent layer can absorb debris or fluids from an inner surface of the cannula and when a viewing scope is received by the lumen, the lens-cleaning portion engages and clears debris from a lens of the viewing scope. In particular configurations, the lumen is radially expandable to accommodate viewing scopes of various diameters.

In a particular iteration, the luminal scaffold layer comprises a resilient mesh that is deformable/expandable and conforms around the viewing scope once the scope is received within the lumen. In a particular embodiment, the absorbent layer is compressible and the luminal scaffold is substantially non-radially deformable. In particular combinations of elements, the luminal scaffold can also be made of an absorbent material, that is, in addition to the absorbent layer. With any of the embodiments, a collar portion can be provided at a proximal portion of said multilayered tube, wherein the collar portion, upon insertion of the cannula and scope cleaning apparatus into a cannula, abuts a proximal portion of a cannula, which can have a cannula collar. In accordance with any of the embodiments taught herein, all or portions of the tube and/or lens-cleaning portions of the apparatus can be radially compressible and/or deformable to fit into cannulas of differing diameters, thereby providing a user with a cannula and scope cleaning apparatus that can be utilized across a variety of cannulas having differing inner diameters, as well as for use with viewing scopes of various outer diameters. That is and in one aspect, the teachings disclosed herein thus provide a cannula and scope cleaning apparatus that is radially conformable, and as such, can be utilized with various combinations of cannulas and viewing scopes, having a range of inner and outer diameters, respectively.

In another aspect, a method for cleaning a cannula and distal end of a viewing scope is disclosed herein, comprising the steps of providing a cannula and scope cleaning apparatus having a tube with an inner surface configured to slidably receive a viewing scope and an outer surface having at least a portion of which is absorbent, where the tube is configured to be slidably received by a cannula at a surgical site, the tube further including a proximal portion, a distal portion and a lumen therethrough, and further includes a lens-cleaning portion coupled to a distal portion of the tube and configured to engage at least a portion of the viewing scope; inserting the cannula and scope cleaning apparatus into the cannula to thus absorb any bodily debris (e.g. fluid, such as blood or other bodily fluid and/or tissue debris), introducing a distal end of the viewing scope into the lumen via a proximal access port; and slidably reciprocating the distal end of the viewing scope with respect to the cannula and scope cleaning apparatus so that at least a portion of the viewing scope engages the lens-cleaning portion, thereby cleaning the viewing scope, in particular the lens of the viewing scope. In a particular step, the cannula and scope cleaning apparatus can be slid onto the viewing scope, after which the combination of viewing scope and the cannula and scope cleaning apparatus disposed thereon is inserted into a cannula.

In still another aspect of the present disclosure, a kit can comprise in, in any combination, a cannula and scope cleaning apparatus configured in accordance with the teachings of the present disclosure, a trocar, and/or a cannula. In one example, the kit can include a cannula and scope cleaning apparatus, and a corresponding cannula, as taught herein, and allows for the use of viewing scopes having different outer diameters with a single cannula having a single internal diameter (of course, viewing scopes will have an outer diameter that is less than the inner diameter of the cannula of the kit in order to fit therethrough); in particular configurations, the radially expandable lumen of the cannula and scope cleaning apparatus as disclosed herein provides stability and support for scopes of various diameters within a particularly sized cannula. In such kits and as taught herein, the cannula and scope cleaning apparatus are provided with an appropriate coupling mechanism to provide securing engagement of the cannula and scope cleaning apparatus to the cannula. In some embodiments, a cleaning fluid for cleaning and/or reducing condensation of a viewing scope lens is also included in the kit in order to preload the absorbent tip of the cannula and scope cleaning apparatus before use, if so desired.

Thus and in accordance with one aspect of the teachings provided herein, a cannula and viewing scope may be cleared/cleaned of bodily tissue and/or fluid deposited within a cannula and/or on a lens of a viewing scope. As previously discussed, such deposition may arise as a result of the removal of a trocar from a trocar/cannula combination (that is, after initial insertion of a trocar/cannula combination into a patient and withdrawing the trocar therefrom, thus leaving the cannula inserted into the patient to provide access to an internal patient location, such as, for example, a joint location, an abdominal location or thoracic location); and/or arise from the insertion/manipulation/removal of instruments, such as the viewing scope, within the cannula, as well as obstruction of a viewing scope lens occurring at a surgical site within the patient during a medical procedure.

DETAILED DESCRIPTION

Described herein is a system and method for cannula and scope cleaning apparatus and associated methods of use. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1A:
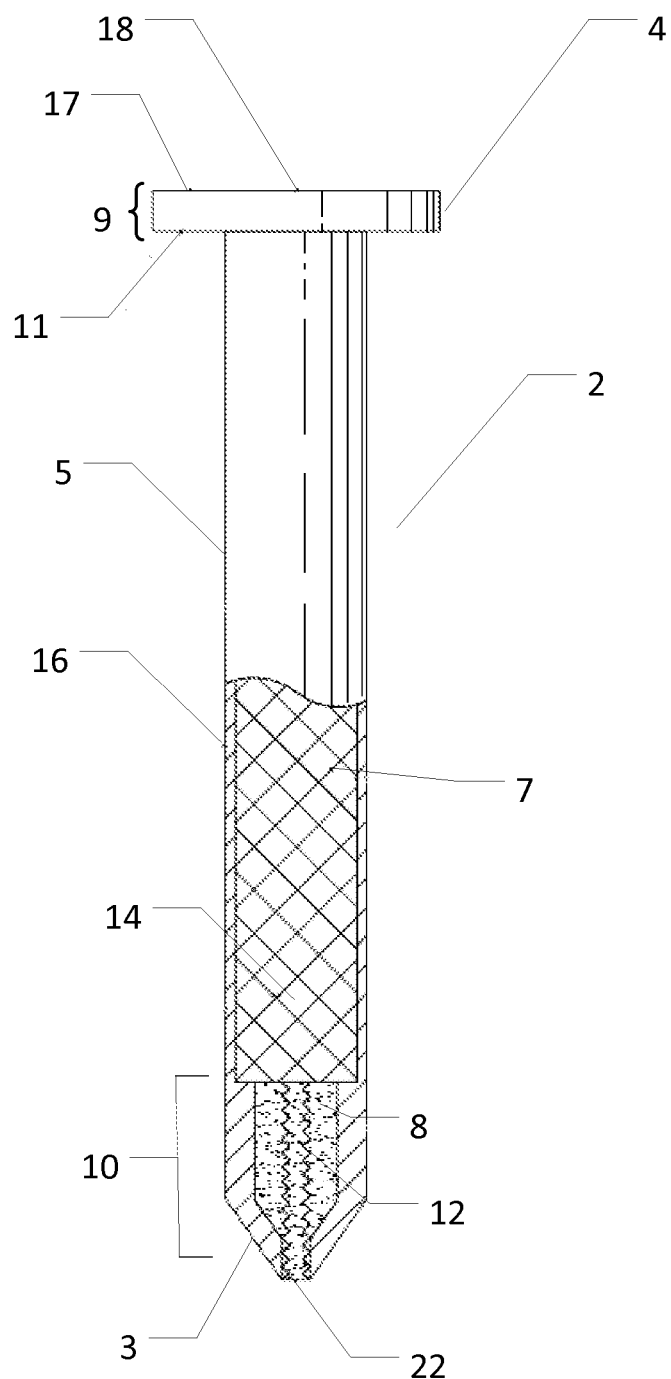
FIG. 1A illustrates a partial cross-sectional side view of one embodiment of a cannula and scope cleaning apparatus.

FIG. 1A illustrates an exemplary configuration of a cannula and scope cleaning apparatus 2 is shown in accordance with particular aspects and teachings provided herein. The cannula and scope cleaning apparatus 2 can comprise a tube 5, for example, which can be provided comprising a single layer or multiple layers (i.e., comprising at least two layers) along its length, having a proximal portion 9, a distal portion 10 and a lumen 14 therethrough. Tube 5 can have an inner surface and an outer surface of which at least a portion of one or both is absorbent. Absorbency of the outer surface, and/or inner surface of tube 5 can be provided by, for example, an absorbent layer 16, which can include and terminate at an absorbent tip 3. As an example of a material from which absorbent layer can be provided, a layer of hydrophilic open cell foam, such that it is wettable, and absorbs water can be utilized. Examples of such open cell foam are described in U.S. Pat. No. 7,175,021 filed Dec. 23, 2003, which is herein incorporated by reference in its entirety. In one or more preferred embodiment, such open cell foam layer is made from a resin selected from the group consisting of polyethylene, polyvinyl chloride, polyacrylonitrile (such as the "BAREX" resin sold by the British Petroleum/Amoco company), poly(ethylene terephthalate), polystyrene, rubber-modified polystyrene, Kraton Polymers supplied by Kraton, ethylene vinyl acetate (EVA), mixtures of polystyrene and EVA, ethylenepolystyrene, interpolymers (such as "INDEX" interpolymers sold by Dow Chemical Corporation of Midland Mich.), polypropylene, polyurethane, polyisocyanurate, epoxy, urea formaldehyde, rubber latex, silicone, fluoropolymer or copolymers thereof or blends thereof. Additional useful adsorbent materials are disclosed in U.S. Pat. No. 4,985,467 filed Apr. 12, 1989; U.S. Pat. No. 4,076,663 filed Mar. 29, 1976 and U.S. Pat. No. 7,291,382 filed Sep. 24, 2004, all of which are herein incorporated by reference in their entireties. Additional exemplary absorbent materials that absorbent layer 16 can be comprised of include, but not limited to, nylon, polycaprolactam, cotton (such as spun cotton, for example) or gauze (which can be provided with a plastic porous film such as polyethylene terephthalate or a polyblend on its outer and/or inner surface) and blends of cotton/polyester or absorbent particulates (such as superabsorbent polymers (SAP), hydrogels), particulate water-absorbent resin (e.g. U.S. Pat. No. 7,285,615 filed Aug. 27, 2004 and herein incorporated by reference) or any combination thereof for example.

In one embodiment, absorbent layer 16 can comprise any suitable material, such as rubber, that will allow absorbent layer 16 to squeegee the inner wall of a cannula, dispelling liquids and other materials outside. In such embodiment, it is not necessary that absorbent layer 16 actually absorb any material.

Proximal portion 9 of apparatus 2 can include a collar 4 and further, a proximal access port 18, through which surgical instruments, such as a viewing scope 26, are slidably introduced into lumen 14 and pass therethrough to, and eventually through, distal portion 10 of the apparatus 2. Collar 4 can have a proximal top surface 17 and a distal bottom surface 11. In this embodiment, apparatus 2 further comprises a lens-cleaning portion 8 coupled to tube 5. Lens-cleaning portion 8 can be comprised of a resilient material, such as an elastomer. Elastomer refers to material having elastomeric or rubbery properties. Elastomeric materials, such as thermoplastic elastomers, are generally capable of recovering their shape after deformation when the deforming force is removed. Specifically, as used herein, elastomeric is meant to be that property of any material that, upon application of force, permits that material to be stretchable and/or compressible and/or expandable to a stretched and/or compressible and/or expanded configuration, after which when such force is removed, the material recovers its previous configuration. Many elastomeric materials may be deformed by much more than 50 percent of their initial length/shape, and many of these will recover to substantially their original relaxed length upon release of the deformation force. Lens-cleaning portion 8 can be comprised of one or more pieces, one being preferred, and can be coupled to tube 5 by a friction-fit or adhered thereto, utilizing a suitable adhesive (not shown), such as, for example, silicon rubber or a waterproof polyepoxide.

In one configuration and as an example, lens-cleaning portion 8 can have, along a passageway therethrough and to opening 22, scrubbing elements 12 along a portion or along its entire passageway. Such scrubbing elements 12 can be provided in any useful configuration, such as in rows or in a spiral configuration, for example, in order to provide and promote a scrubbing effect to remove unwanted condensation and debris from a lens 24 of a lens portion of a viewing scope 26 when the lens is passed reciprocally and/or rotated within lens-cleaning portion 8. Scrubbing elements 12 can be embodied by any raised portion having any useful shape, such as ribs, ridges or bumps and crevices, for example. Lens-cleaning portion 8 can have, as shown in other embodiments, a smooth passageway therethrough, which can also provide a wiping action to clear lens 24 of a viewing scope 26. When viewing scope is passed therethrough, the edges of the passageway, which can be provided by an annular opening or a slit, as discussed below, will swipe over the lens 24 of viewing scope 26 to remove debris such as bodily fluids, condensation, and other debris that may cover lens 24 of viewing scope 26. In particular embodiments, lens-cleaning portion 8 can be provided loaded with a cleaning solution, such as FRED antifog solution or any appropriate aqueous solution containing alcohol and/or surfactant, for example, to reduce/eliminate condensation of a viewing scope lens.

Absorbent tip 3 can be shaped to decreases in diameter toward opening 22, for example, such that introduction of the cannula and scope cleaning apparatus 2 into a cannula (not shown) is facilitated. As one example, absorbent tip 3 can be conically shaped, but other shapes are also contemplated, such as a pyramidal or square shape, for example. Absorbent tip 3 can be provided and made from the same or different material from which absorbent layer 16 of tube 5 is made from. By providing an absorbent tip 3, the cannula and scope cleaning apparatus 2 of the present disclosure is able to absorb and clear debris, such as a fluid (e.g. bodily fluid such as blood and/or tissue) that is typically found within a cannula 28 after insertion of a cannula into a patient. Cannulas are typically so disposed by their use in conjunction with a trocar located therein. Once the cannula/trocar combination is introduced, the trocar is then withdrawn, leaving debris along its withdrawal pathway within the cannula. Such debris is then typically picked up by the lens 24 of the subsequently introduced viewing scope 26. By providing absorbent tip 3 of cannula and scope cleaning apparatus 2 as taught herein, such debris is thus absorbed and cannot contaminate lens 24 when viewing scope has cannula and scope cleaning apparatus 2 disposed upon viewing scope 24 and in combination, are introduced into cannula 28, which is inserted through the a patient. In addition, absorbent layer 16 provides for additional assurance that any such debris not addressed by absorbent tip 3 upon insertion of cannula and scope cleaning apparatus 2 into cannula 28, is absorbed by absorbent layer 16, thus clearing/cleaning the cannula of initial trocar-introduced debris and subsequently maintaining this state throughout the surgical procedure.

In various embodiments, the cannula and scope cleaning apparatus 2 can include luminal scaffolding, that is, luminal support structure that helps to maintain integrity, such as circumferential integrity, of lumen 14, and/or provide for radial expansion so as to provide for dilatation of lumen 14 so as to provide for a snug fit around instruments, such as a viewing scope 26 introduced therein, over a range of outer diameters of the introduced instruments. As represented in FIG. 1, a luminal scaffold can be provided by a mesh 7, which can be of radially deformable/expandable material or can be provided of a substantially non-expandable material. Mesh 7 can, for example, line lumen 14, as depicted in FIG. 1 and/or be provided as part of, and integrated into, absorbent layer 16. When luminal scaffold, such as mesh 7, is to be radially expandable, absorbent layer 16 can accordingly be radially expandable and/or compressible in order to slidably receive a surgical instrument, such as viewing scope 16, into lumen 14.

Mesh 7 is made of suitable materials such as medical grade polymers, for example polyethylene terephthalate, which can be braided and is radially expandable, expanding when a viewing scope 26, for example, is inserted into the cannula and scope cleaning apparatus 2 disposed therein. For example and not limitation, mesh 7 can be a braided tube and be formed in a variety of ways, but in one embodiment it can be formed by interweaving a plurality of filaments around a central mandrel via a braiding machine. The interwoven braided filaments can be spaced so as to allow the filaments to move relative to each other. The term "filament" as used herein is broadly defined to cover any element with an elongated configuration, including but not limited to a thread, fiber, cord, string, yarn, twine, rope, line, cable, wire, ribbon, tape, or the like. The filaments may all be the same type and material, or a composite of different of types or materials. By way of non-limiting example, a maypole type of braiding machine, as sold by Steeger USA, Inc. of Spartanburg, S.C., or by the New England Butt Division of Wardwell Braiding Machine Company, can be used in construction of mesh 7. A person of ordinary skill in the art will appreciate that braiding machines of this type use two groups of carriers, where each carrier carries a spool of the filament to be presented by the respective carrier. Carriers are arranged in a circular array around a braiding axis of the central mandrel and are driven in one direction about that axis. Carriers of the first group are arrayed around the braiding axis and are driven in clockwise direction for example. Carriers of the second group are also arrayed, in a circular array around the braiding axis, in an alternating order with respect to carriers of the first group, and are driven in the opposite direction about the braiding axis. As the carriers move, the filaments are pulled off their respective spools and laid out onto the central mandrel forming the braided tube. A person skilled in the art will also appreciate any type of machine capable of forming the braided tube can be used in place of a maypole type braiding machine described above.

The filaments used to make the mesh 7 can be formed from a variety of materials. By way of non-limiting example, the filaments can be formed from polyester, cotton, polyamide, polyalkane, polyurethane, PET, PBT, nylon, PEEK, PE, glass fiber, metal wire, acrylic materials, and the like, or any composition of the mentioned materials. They may be in the form a monofilament or a multifilament and may have a cross section in the shape of any geometrical form, such as a cross section in the form of a rectangle, square or a circle. A person skilled in the art will appreciate that the porosity of the mesh 7 and the size of the windows (i.e., the spaces between the interlaced filaments) formed by the intersecting filaments are a function of the perpendicular distance (d) between the parallel filaments, the thickness of the filaments, and the intersection angle (A). The arrangement of the filament braiding will change the characteristics of the braided flexible tube. For example, the porosity of mesh 7 influences its flexibility and its hoop strength. For instance, if all other variables are held constant, the lower the porosity of a braided tube then the higher its hoop strength becomes.

Decreasing the initial intersection angle (A), increasing the thickness of the filaments or their numbers, and decreasing the perpendicular distance between the parallel filaments are all ways to reduce the porosity of the braided flexible tube. Methods for making such radially expandable braided tubes are disclosed in U.S. Patent Application Publication No. US 2009/0082731 A1, filed Sep. 20, 2007 and in U.S. Patent Application Publication No. 2003/0216770 A1, filed Feb. 20, 2003, both herein incorporated by reference in their entirety. In another particular configuration, it is contemplated that luminal scaffold can be configured as a spiral luminal scaffold (spring-like configuration) around which absorbent layer 16 is disposed. Such a configuration provides for flexibility along the length of cannula and scope cleaning apparatus 2, useful for use with viewing scopes and/or cannulas that can be flexible, if so desired.

Figure 1B:
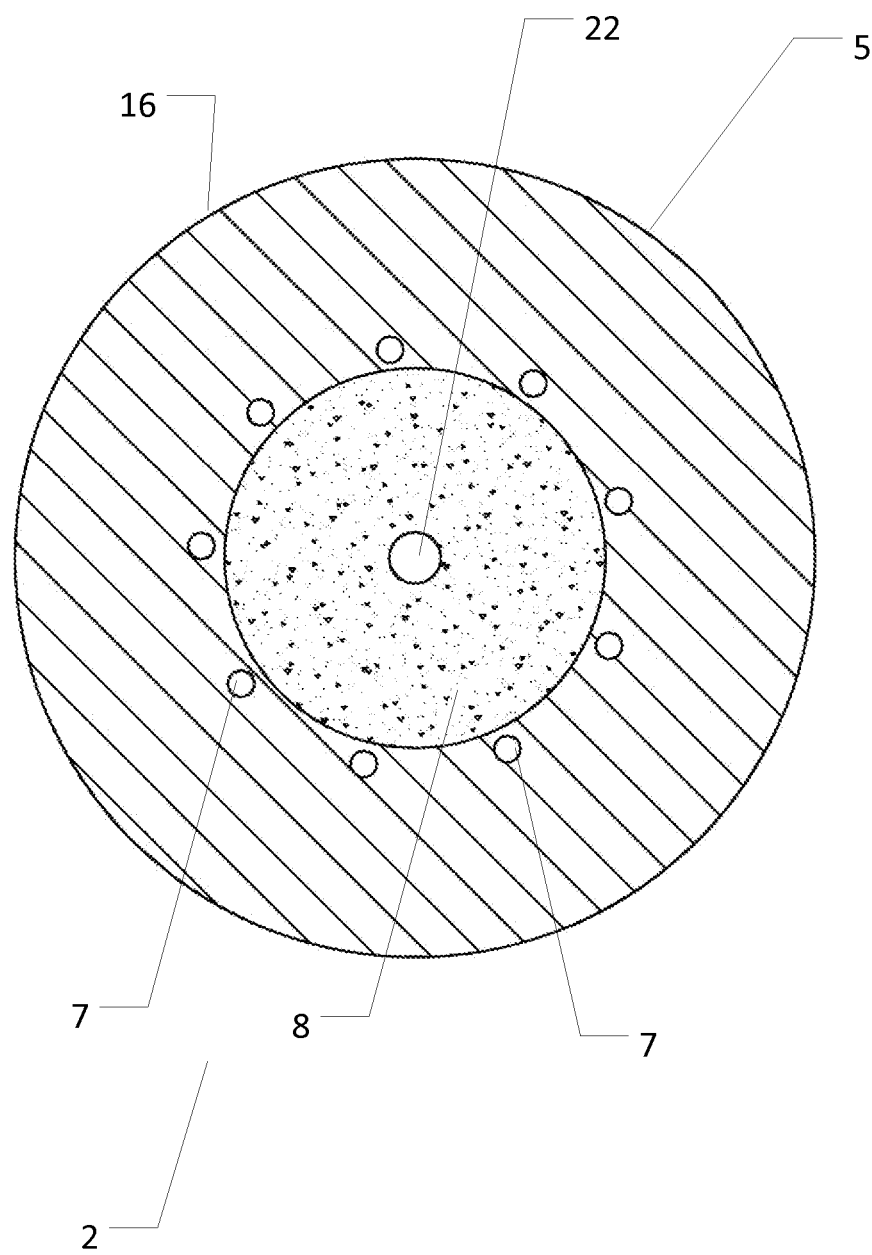
FIG. 1B illustrates a section view of an embodiment in accordance with the teachings provided herein, taken generally along the line 6a in FIG. 1A.

FIG. 1B illustrates a section view of an embodiment in accordance with the teachings provided herein is shown, taken generally along the line 6a in FIG. 1A. Opening 22 of lens-cleaning portion 8 is centrally shown, where lens-cleaning portion 8 has a lens-cleaning portion thickness $t_2$ (scrubbing elements 12 not shown).

Figure 2:
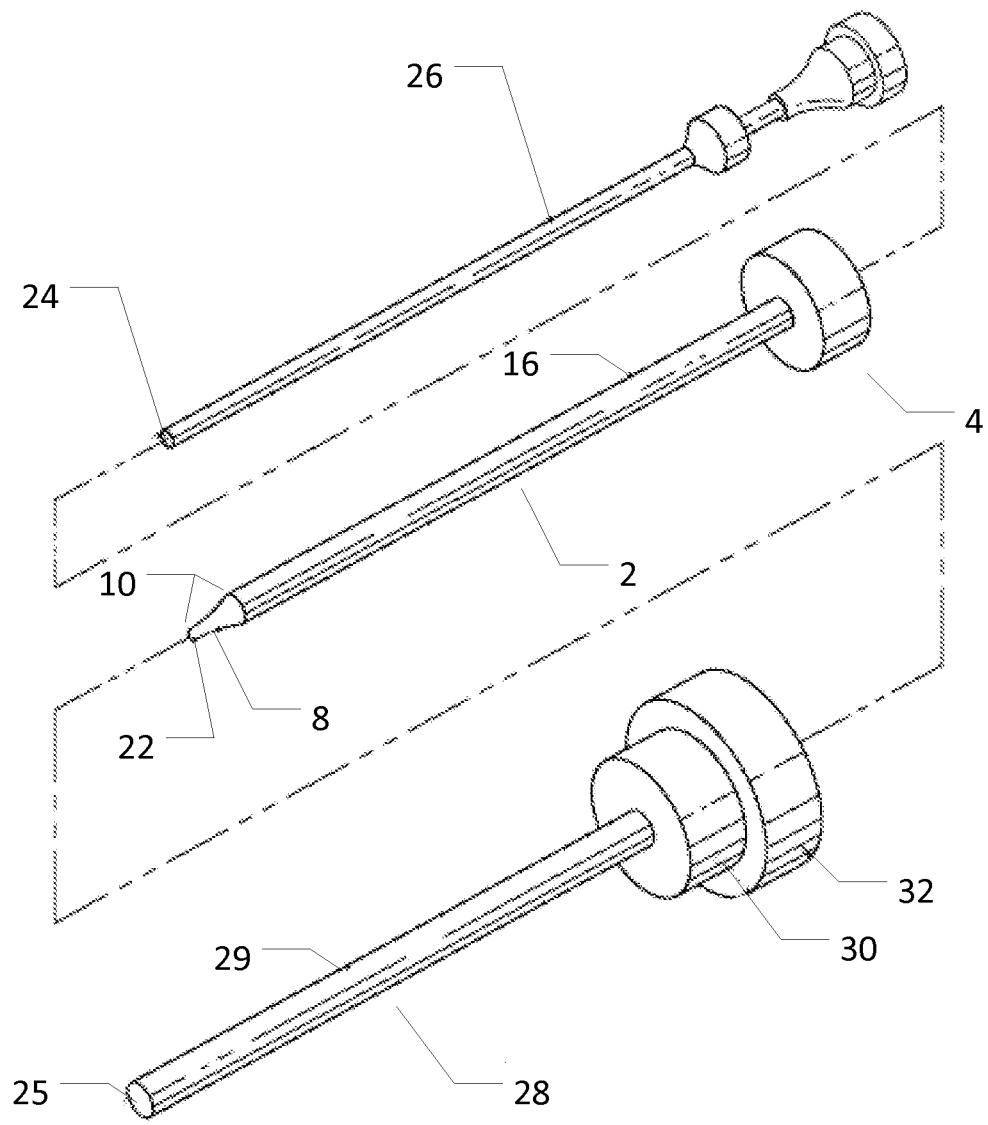
FIG. 2 illustrates an example of a viewing scope, an embodiment of a cannula and scope cleaning apparatus and a cannula.

FIG. 2 depicts a viewing scope 26 with a lens portion having lens 24, an embodiment of cannula and scope cleaning apparatus 2 with absorbent layer 16 and lens-cleaning portion 8, and a cannula 28 with a cannula shaft 29, cannula distal opening 25, cannula collar 32 and insufflation valve portion 30.

Exemplary viewing scopes 26 for are of two basic types, those with and those without an operative channel, and typically range in size from about 3 mm to 12 mm, and have either straight or angled lenses. A 0-degree lens provides a panoramic view while angled 30-, 45-, and 135-degree lenses assist in evaluating the anterior of a patient, such as the abdominal wall or working around masses. The larger the caliber of the viewing scope 26, the greater the number of fiber bundles contained therein, and the higher the quality of the video picture. A viewing scope having a lens of any degree can be utilized in accordance with the cannula and trocar cleaning apparatus 2 of the present disclosure.

Outer diameter $d_1$, of any embodiment of cannula and scope cleaning apparatus 2 can be from about 4 millimeters (mm) to about 20 millimeters or any thickness therebetween, more preferably from about 5 mm to about 15 mm and most preferably from about 8 mm to about 10 mm Inner diameter of a cannula 28 can be from about 3 mm to about 20 mm or any size or range therein between. "About" means approximately or nearly and in the context of a numerical value or range set forth herein means+1-15% of the numerical value or range recited or claimed. Absorbent layer thickness $t_1$ (wall thickness) of absorbent layer 16 can be from about 1 mm to about 9 mm or any thickness therebetween, more preferably from about 2 mm to about 7 mm. Lumen diameter $d_2$ can be from about 3 mm to about 15 mm, depending of course on the overall outer diameter $d_1$ and absorbent layer thickness $t_1$, which will define lumen diameter $d_2$. Of course, where absorbent layer 16 is made of a compressible material, as discussed above, lumen diameter $d_2$ will increase when and according to the outer diameter of the viewing scope 26 disposed therein. Likewise, outer diameter $d_1$ will decrease if cannula and scope cleaning apparatus 2 is larger than an internal diameter of a cannula 28, and as such is compressed upon insertion to cannula 28. This flexibility afforded by the use of compressible absorbent materials to make tube 5 provides for the use of a single size cannula and scope cleaning apparatus 2 with a multitude of cannulas and viewing scopes having various combinations of internal and external diameters, respectively, thus providing the cannula and scope cleaning apparatus 2 of the present invention the ability to be readily utilized with cannulas and/or viewing scopes or various sizes, depending upon those available at a particular surgical facility.

Referring back to FIG. 2, cleaning portion thickness $t_2$ can be provided such that lens-cleaning portion 8 offers sufficient resistance to the passage of the viewing scope 26 so that a user easily determines, by feel of resistance, when contact between a distal end of viewing scope 26 and the lens-cleaning portion 8 has been reached. Subsequently, a user can engage lens 24 of viewing scope 26 against lens-cleaning portion 8 by, for example, rotating and/or otherwise reciprocally maneuvering lens 24 against the lens-cleaning portion 8 in order to clean lens 24.

Figure 8:
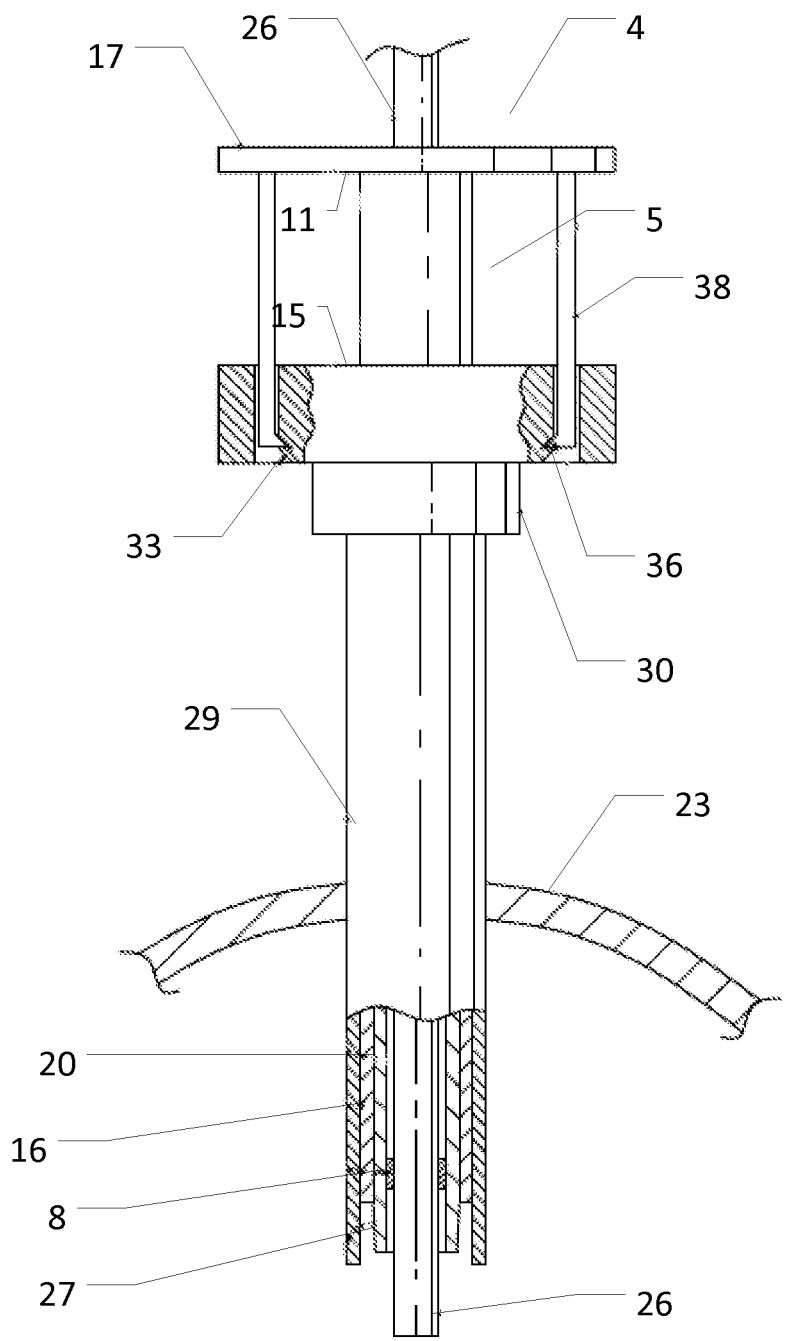
FIG. 8 illustrates an exemplary cannula and trocar cleaning apparatus embodiment is retracted and coupled to a cannula.
Figure 11A:
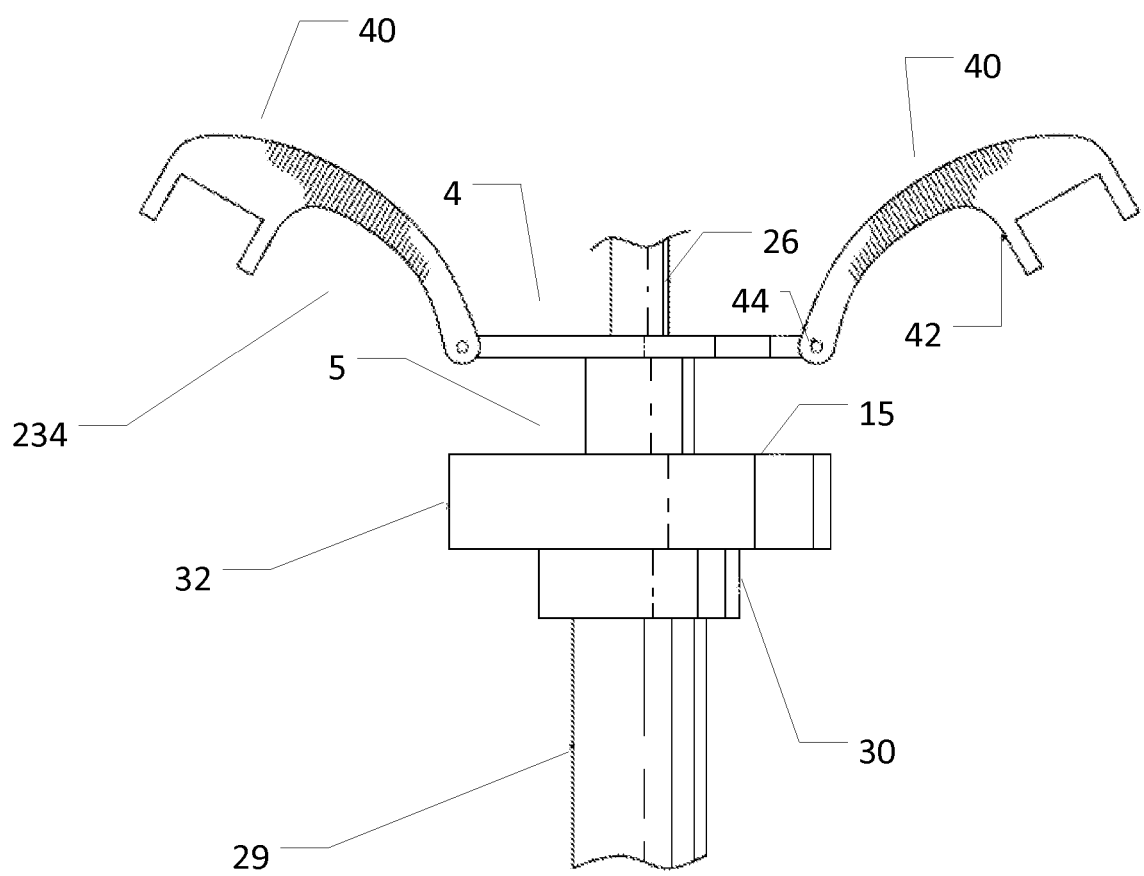
FIG. 11A illustrates yet another embodiment of an exemplary coupling mechanism, before coupling, to a cannula.

Cannula and trocar cleaning apparatus 2 has an outer diameter $d_1$, and a lumen diameter $d_2$. Furthermore and as shown in this example, filaments of mesh 7 are radially disposed about lumen 14 and absorbent layer 16 has an absorbent layer thickness $t_1$. According to various embodiments, the cannula and trocar cleaning apparatus 2 is an elongate rigid structure sized to be slidably inserted into the lumen of a cannula while simultaneously being able to receive therein a viewing scope 26 within lumen 14. Accordingly, as generally shown in FIGS. 5, 8, 11A, B and 12A, B the cannula and trocar cleaning apparatus 2 can be sized as to be interposed between the cannula 28 and viewing scope 26, for example, in a nested arrangement of components.

Figure 3A:
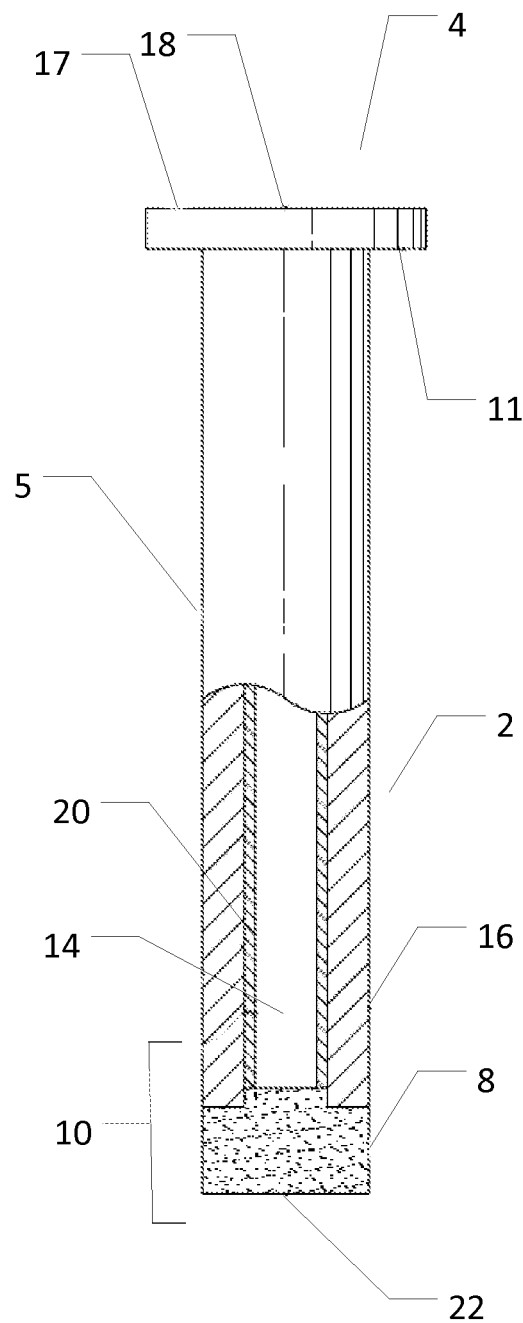
FIG. 3A illustrates a partial cross-sectional side view of a second embodiment in accordance with the teachings provided herein.

FIG. 3A illustrates an embodiment of cannula and scope cleaning apparatus 2 similar to the embodiment shown in FIG. 1. It is to be noted that the luminal scaffolding elements, along with all various elements and features illustrated or described in connection with one exemplary embodiment, may be combined with the features of other embodiments provided by the teachings herein disclosed. For example, mesh 7, which can be radially expandable, can be utilized as luminal scaffolding in the embodiment depicted in FIG. 2, as well as in all other embodiments, provided, naturally, that absorbent layer 16 can be accordingly expandable compressible. Notably in this embodiment, luminal scaffold can be provided by a substantially non-radially deformable scaffold layer 20, and as shown in distal portion 10, lens-cleaning portion 8 has an outer diameter that is substantially the same as the outer diameter of tube 5, as depicted here. As lens-cleaning portion 8 can be made from a resilient material, such as an elastomer, in this embodiment where lens-cleaning portion 8 has an outer diameter that is substantially the same as the outer diameter of tube 5, lens-cleaning portion 8 provides for a good friction fit and seal between cannula and scope cleaning apparatus 2 and the cannula 28, once the apparatus 2 is slidably received by cannula.

Figure 3B:
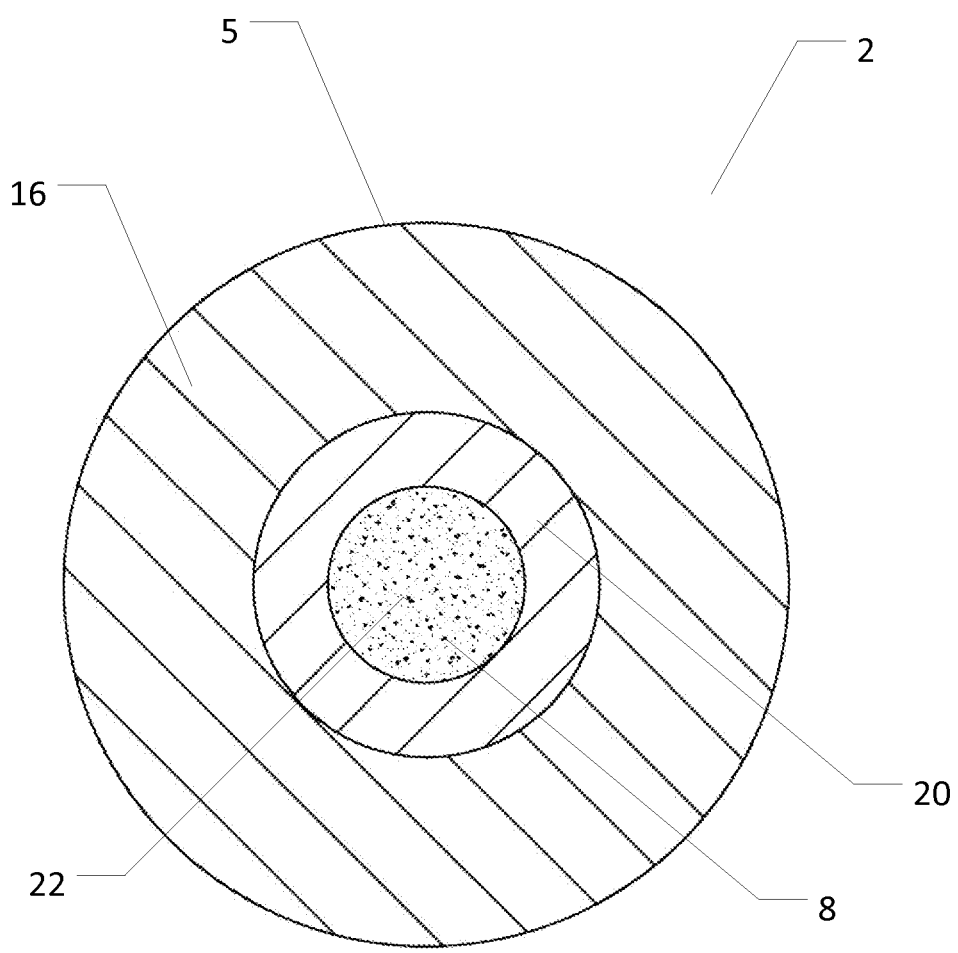
FIG. 3B illustrates a section view of an embodiment in accordance with the teachings provided herein, taken generally along the line 6b in FIG. 3A.

FIG. 3B illustrates a section view taken along line 6b of the embodiment shown in FIG. 3A. In this embodiment, opening 22 can be a slit. Non-radially deformable scaffold layer 20 can be comprised of linear low-density polyethylene (LLDPE), polyvinyl chloride or other suitable materials, such as acrylonitrile butadiene styrene, high-density polyethylene (HDPE) and other medical grade plastics. Such a substantially non-radially deformable scaffold layer can be obtained from any medical tubing manufacturer, such as A.P Extrusion of Salem, N.H., USA. It is to be noted that cannula and trocar cleaning apparatus 2 can even be provided having three layers (not shown), for example having a rigid layer (made of a metal or alloy or plastic) disposed between scaffold layer and absorbent layer, for example, where one of or both of scaffold layer and absorbent layer are radially compressible.

As one example, where absorbent layer 16 is an open foam and a luminal scaffold 20 is a stiff lubricious polystyrene foam, such multilayers of tube 5 can be joined by utilizing a solvent that will partially dissolve or soften both absorbent layer 16 and luminal scaffold 20. With the mating surfaces of absorbent layer and luminal scaffold partially dissolved and in a liquid or plastic state, when such surfaces of absorbent layer and luminal scaffold are engaged with each other, a strong bond there between is provided after the evaporation of the solvent occurs. In one example of such an embodiment, a luminal scaffold 20 of polystyrene closed cell foam is bonded to an absorbent layer 16 comprised of polystyrene open cell foam with 70% open cells by use of a mixture of ortho-, meta-, and para-xylerrnes. Other suitable bonding solvents include acetone, and mixtures of xylenes and methyl alcohol, or similar solvents that at least partially dissolve polystyrene. Use of appropriate solvents with appropriate plastics/foams for bonding one to the other, as described, will be known to those of ordinary skill in the art and can be utilized to bond absorbent layer 16 to luminal scaffolding. Absorbent layer can be joined to luminal scaffold by a suitable liquid or molten adhesive (not shown) applied to outermost surface of luminal scaffold and/or inner surface of absorbent layer 16 prior to engagement with absorbent layer, or by heat seal means, or by application of a double sided adhesive tape (not shown) to outer surface of luminal scaffold 20, for example, prior to the engagement of absorbent layer 16 to luminal scaffold 20. It is contemplated that medically suitable lubricant, such as surgical lubricant, may be utilized, if needed, for smooth passage of the scope within cannula and scope cleaning apparatus 2, as the apparatus of the instant disclosure may be utilized with viewing scopes of differing diameters and outer surfaces.

Non-radially deformable scaffold layer 20, or any luminal scaffold layer as disclosed herein, can have a luminal scaffold thickness $t_3$. Luminal scaffold thickness $t_3$ is typically less than absorbent layer thickness $t_1$, although they can be substantially equivalent in particular embodiments, dependent of course if a particular sized cannula 28 and/or viewing scope 26 combination is utilized, where, for example several cannula sizes are to be utilized with a single scope having a particular diameter. In such a case, luminal scaffold thickness $t_3$ can be fixed and thus lumen 14 size fixed, by utilizing a non-radially deformable scaffold layer 20. That is, by utilizing material is substantially non-compressible in conjunction with an absorbent layer thickness $t_1$ of absorbent layer 16 greater than a luminal scaffold thickness $t_3$, and utilizing a radially deformable/compressible material for absorbent layer 16, cannula and scope cleaning apparatus 2 can be inserted into cannula 28 having a range of inner diameters, while still being able to slidably receive the same sized viewing scope 26.

Figure 4A:
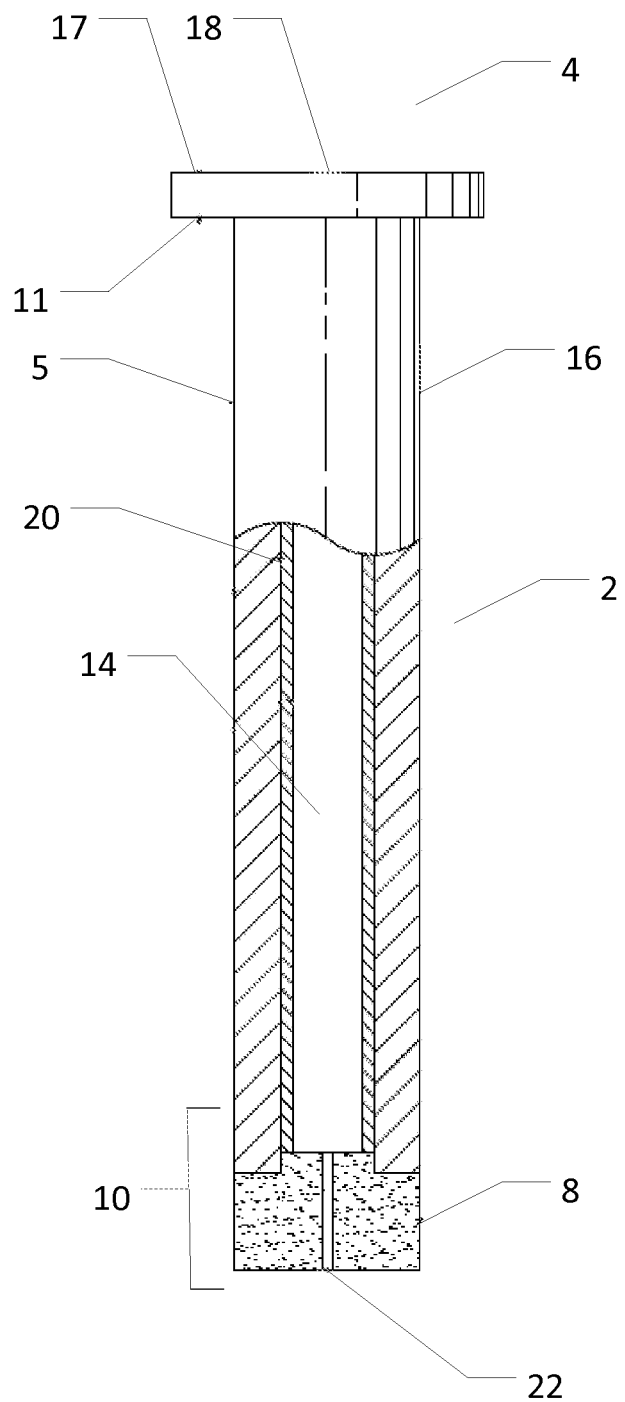
FIG. 4A illustrates a partial cross-sectional side view of a third embodiment according to the present teachings.
Figure 4B:
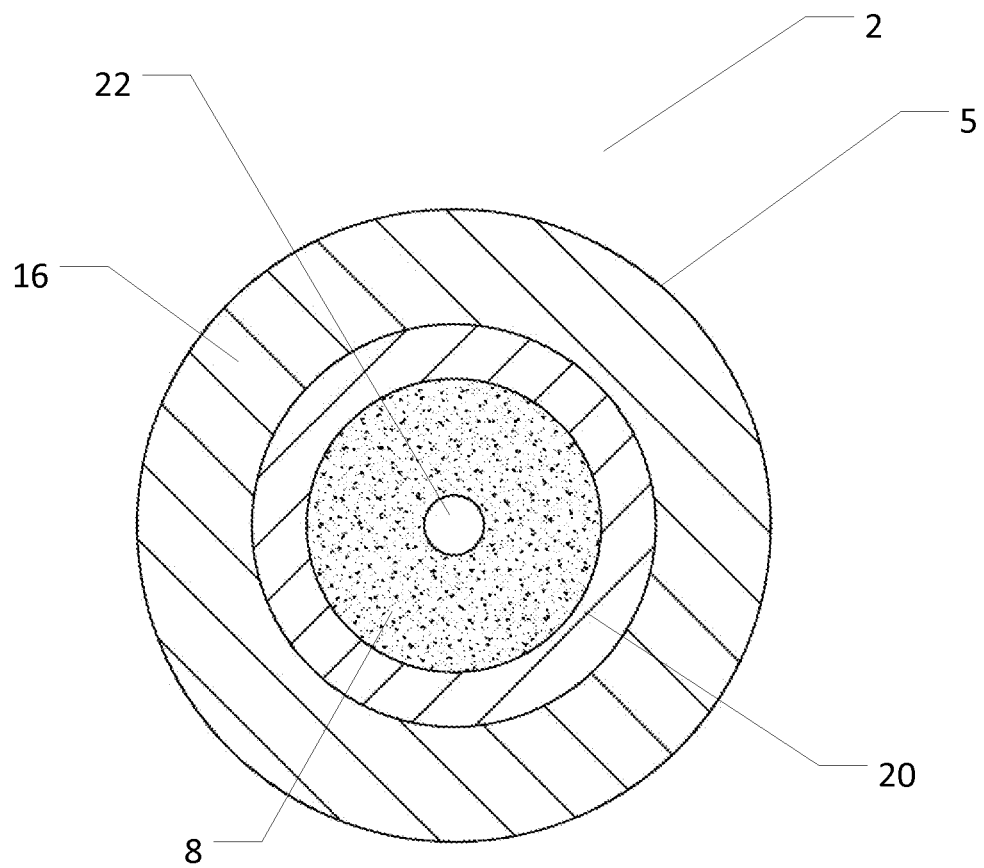
FIG. 4B illustrates a section view of an embodiment in accordance with the teachings provided herein, taken generally along the line 6c in FIG. 4A.

FIG. 4A illustrates another partial cross-sectional side view of a third embodiment according to the present teachings. FIG. 4B illustrates a section view taken along line 6c of the embodiment shown in FIG. 4A. The cannula and scope cleaning apparatus 2 depicted here is substantially similar to that depicted in FIG. 4A, notably here, lens-cleaning portion 8 is shown having a smooth passageway therethrough having opening 22 in an annulus shape, as shown in FIG. 4B.

Figure 5A:
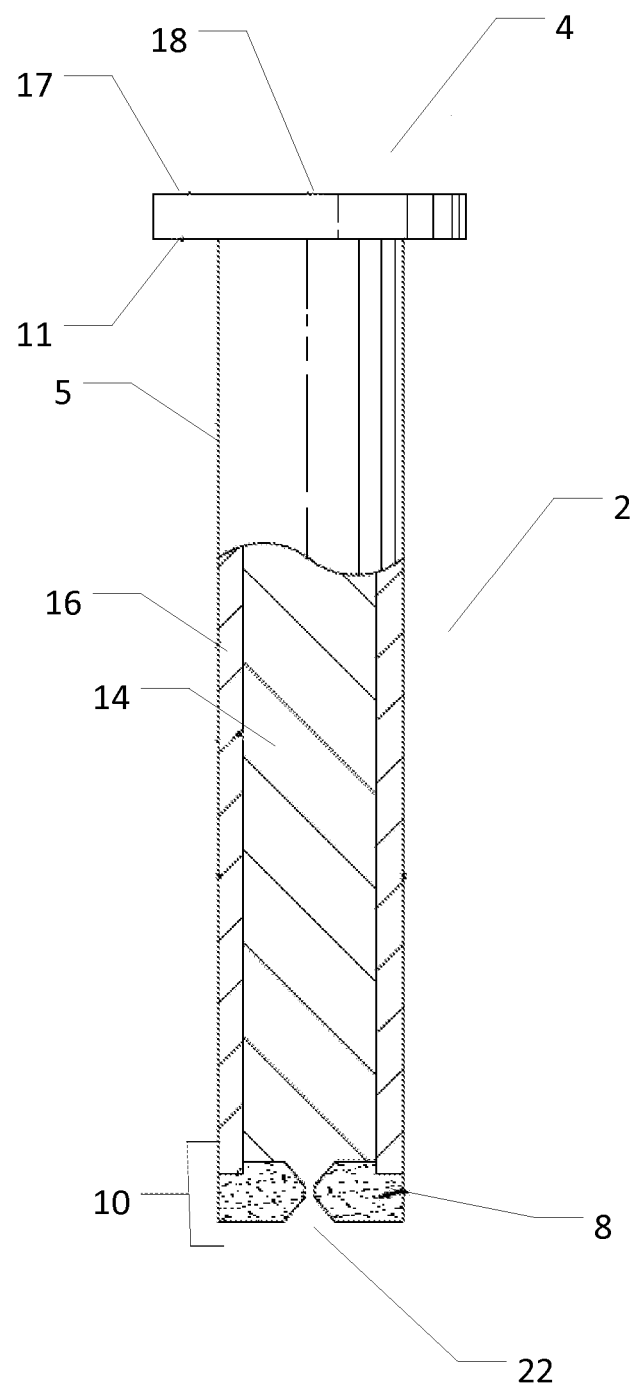
FIG. 5A illustrates a cross-sectional side view of another embodiment according to the present teachings.

FIG. 5A illustrates another embodiment, comprising tube 5 that is a single-layer. Here tube 5 may or may not include scaffolding, provided that absorbent layer 16 is sufficiently rigid/supportive to accommodate insertion of apparatus 2 into a cannula and slidably receive a viewing scope 26 therein. Another distinction is that lens-cleaning portion 8 can comprise a distal tip 10 that is recessed, as shown in FIG. 5A. Such a configuration can shorten reciprocation of viewing scope 26 therethrough (as compared to other exemplary shapes of lens-cleaning portion 8) in order to scrub lens 24 of viewing scope 26, that is, a greater number of swipes of lens 24 of viewing scope 26 are achieved using a shorter stroke length of reciprocation of scope 26 through lens-cleaning portion 8.

Figure 5B:
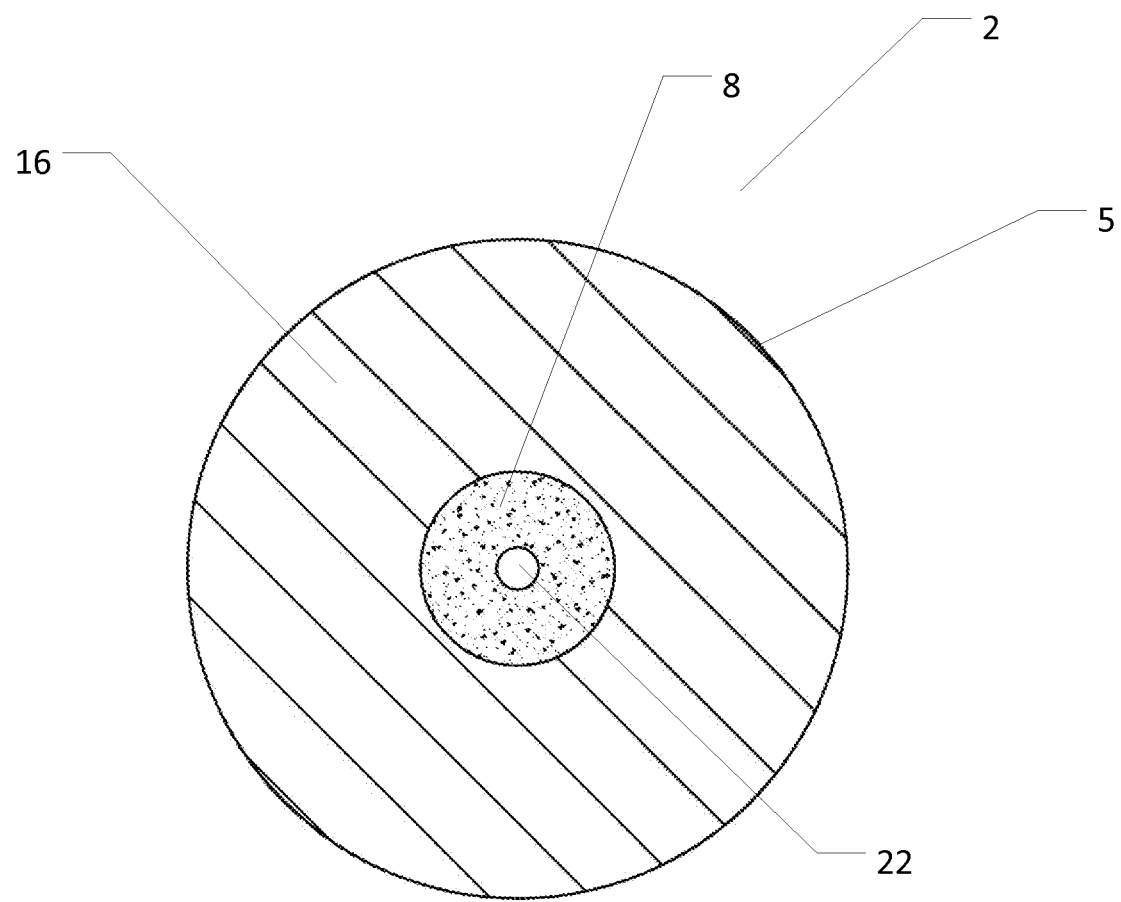
FIG. 5B illustrates a section view of an embodiment in accordance with the teachings provided herein, taken generally along the line 6d in FIG. 5A.

FIG. 5B is a section view of an embodiment in accordance with the teachings provided herein, taken generally along the line 6d in FIG. 5A showing tube 5 comprised of a single layer of absorbent layer 16. Having absorbent layer 16 thus effectively contactable with viewing scope 26 can allow absorbent layer 16 to absorb tissue, bodily fluid, and debris not swiped away by lens-cleaning portion 8, and thus provides for two separate absorption processes to take place, even further decreasing the need for a user to withdraw a viewing scope 26 from within a cannula 28 during a surgical procedure in order to clear/clean lens 24.

Figure 6A:
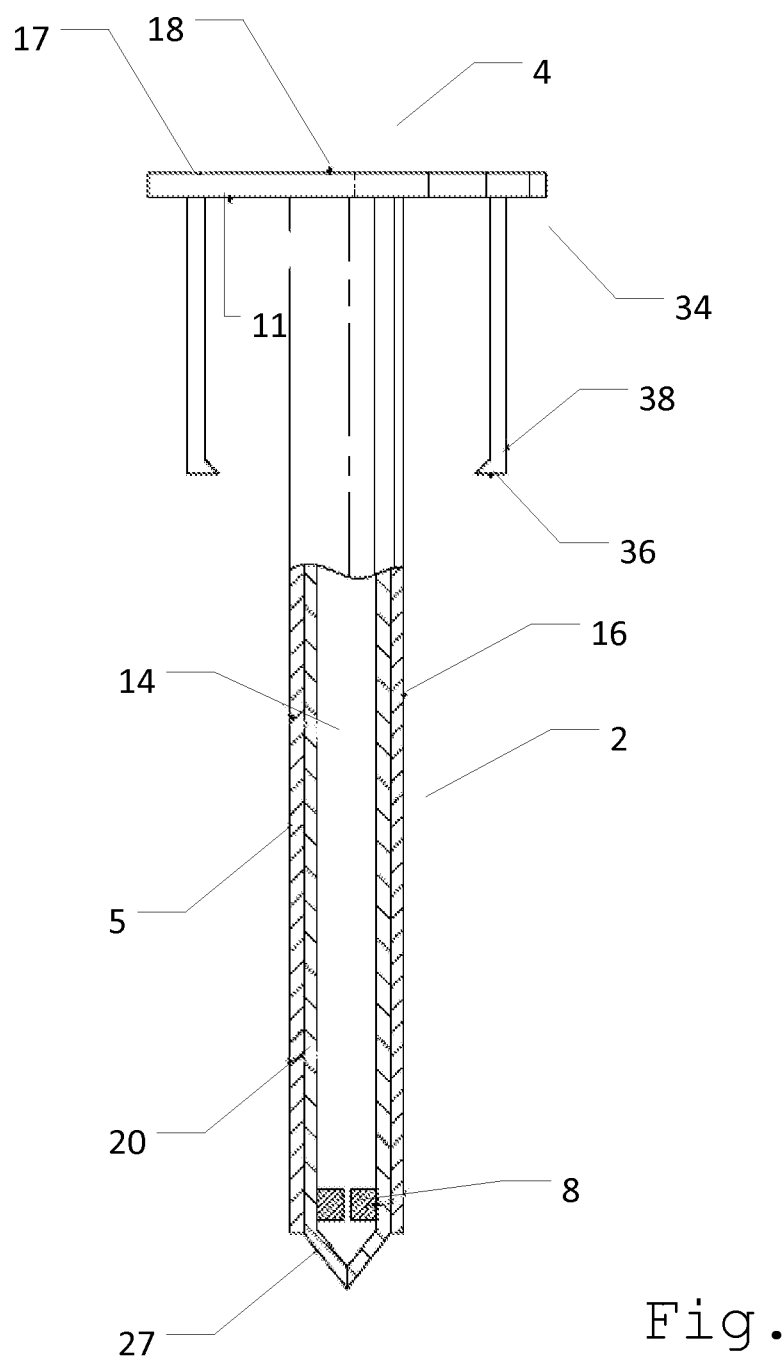
FIG. 6A illustrates another partial cross-sectional view of embodiment in accordance with one configuration.

FIG. 6A, illustrates another embodiment of cannula and scope cleaning apparatus 2 is shown, where collar 4 comprises a cannula coupling mechanism 34, here and in one configuration, extending from collar 4's distal bottom surface 11. In this configuration, cannula-coupling mechanism 34 comprises at least one coupling mechanism extension 38 having a cannula-engaging portion 36. It is additionally noted that scaffold layer 20 in FIG. 6 extends past the distal portion of absorbent layer 16, to end in a tip 27. Tip 27 can be flexible and scaffold layer 20 in this configuration can be made of the same or differing materials. As an example, scaffold layer 20 and tip 27 can be made of plastic or foam which is light transmissible and/or flexible, advantageous characteristics to be discussed in greater detail below. Exemplary thickness of one and/or the other can be from about 0.002 to about 0.1" inches thick. Other exemplary materials include acrylic, linear low-density polyethylene (LLDPE) having thickness of about 0.5, 0.75, 1.0, 1.5, 2.0 and 2.5 mm, polycarbonate or clear flexible vinyl. Materials from which scaffold layer 20 and tip 27 are made in this embodiment are advantageously flexible and can be extruded to a point to form tip 27 which is flexible and resilient to allow for viewing scope 26 to pass through. Also depicted in FIG. 6A is lens-cleaning portion 8 at the distal end of multilayered tube 5. Use of this embodiment of cannula and scope cleaning apparatus 2 is shown in FIGS. 7 and 8.

Figure 6B:
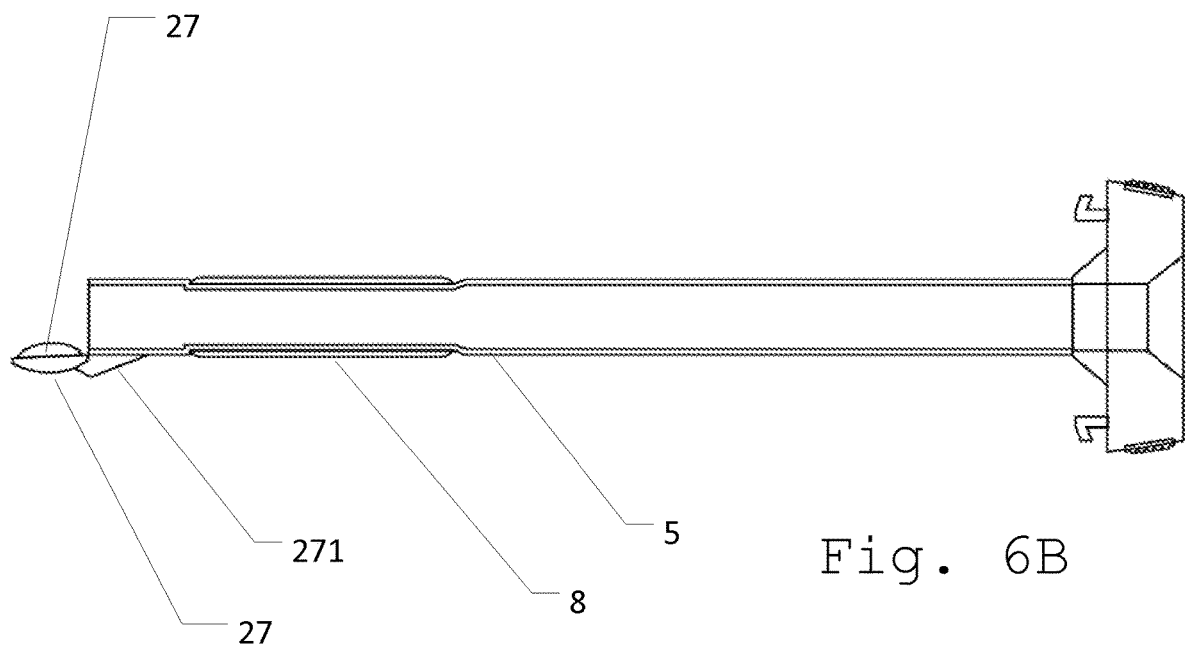
FIG. 6B illustrates a collar comprising a hinged tip in an open position.
Figure 6C:
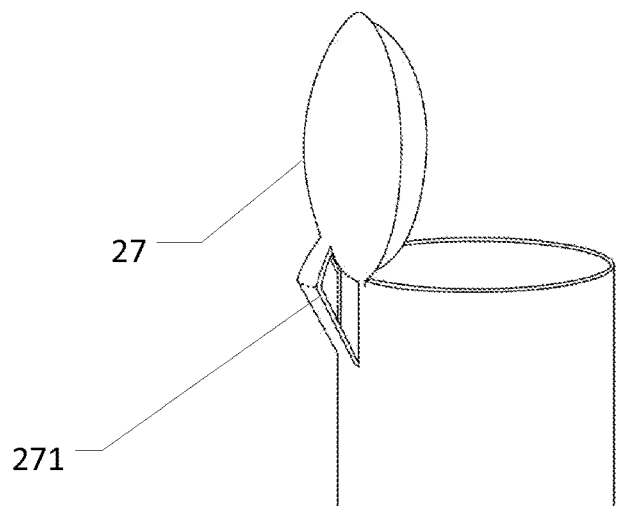
FIG. 6C illustrates a close-up view of a hinged tip in an open position.
Figure 7:
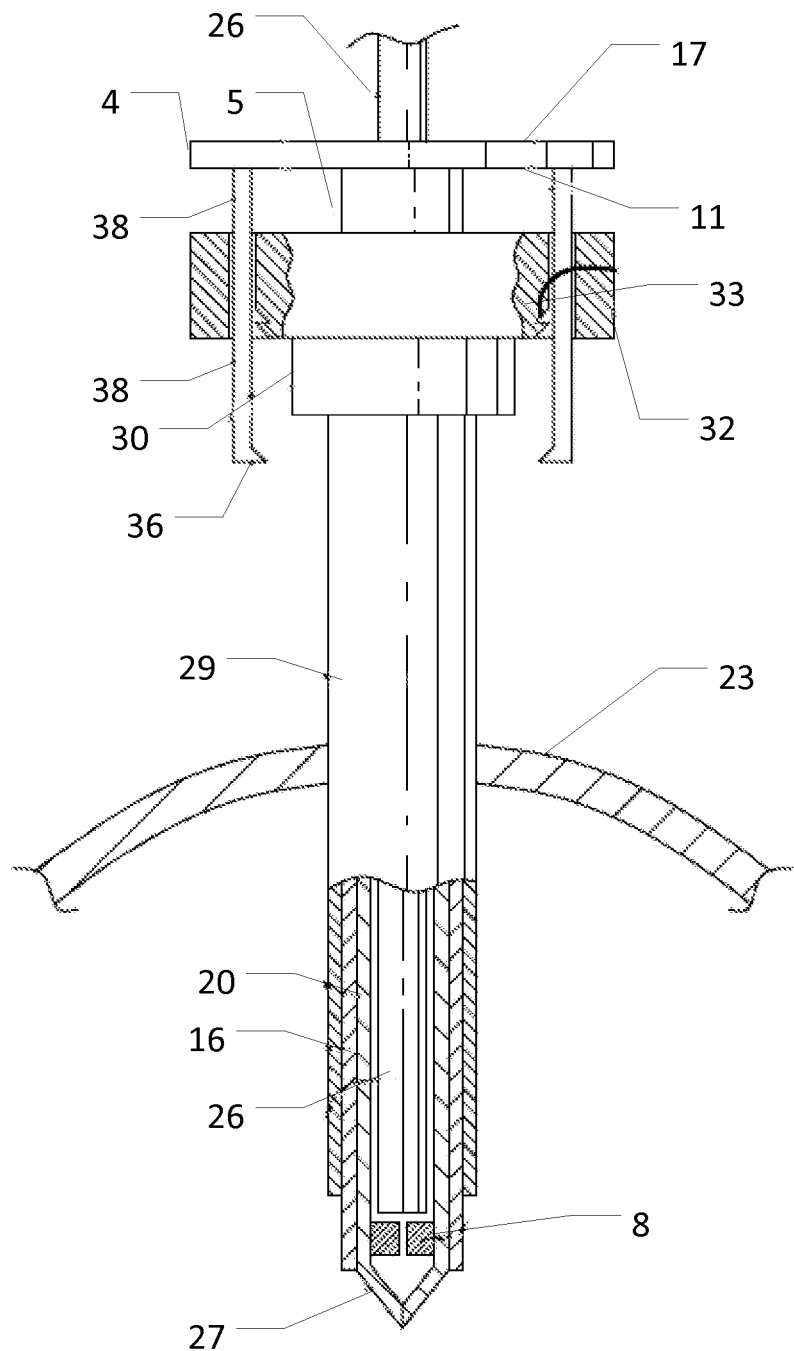
FIG. 7 illustrates a partial cross-sectional view of an embodiment in accordance with the teachings provided herein, showing an exemplary cannula and trocar cleaning apparatus in communication with an exemplary cannula, the cannula and trocar cleaning apparatus protecting a viewing scope as it passes through the cannula and into a subjects body.

FIG. 6B illustrates collar 4 comprising tip 27 attached to tube 5 by a hinge 271, in an open position. FIG. 6C illustrates a close-up view of tip 27 with hinge 271 in an open position. As viewing scope 26 passes through tube 5, viewing scope can push tip 27 such that hinge 271 moves to an open position. In one embodiment, hinge 271 can be biased to a closed position. In one embodiment, tip 27 can comprise lens cleaning portion 8 on the inside portion and/or outside portion of tip 27.

Figure 6D:
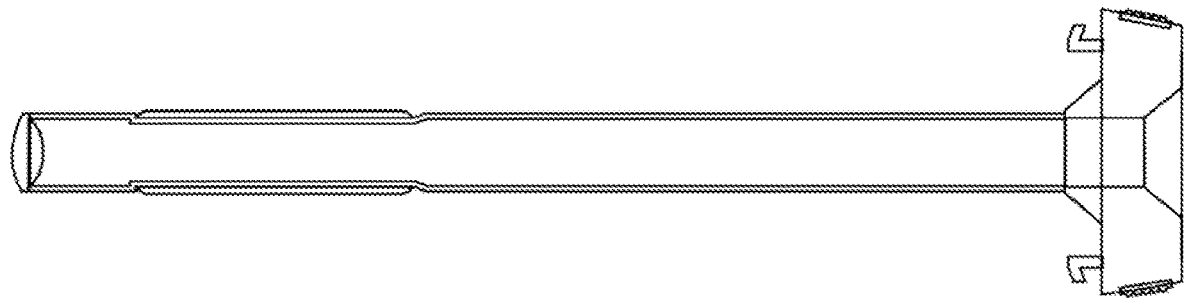
FIG. 6D illustrates a collar comprising a hinged tip in a closed position.
Figure 6E:
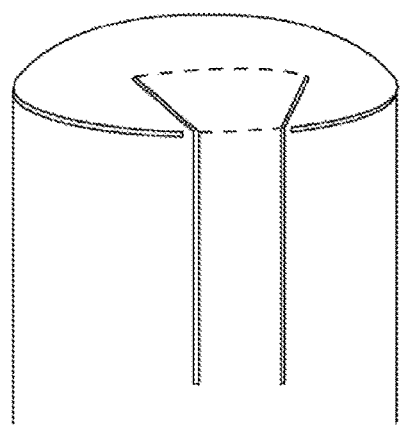
FIG. 6E illustrates a close-up view of a hinged tip in a closed position.

FIG. 6D illustrates a collar comprising tip 27 and hinge 271 in a closed position. FIG. 6E illustrates a close-up view of a hinge 270 in a closed position. As viewing scope 26 passes back through tube 5, hinge 271 can move from an open position as shown in FIG. 6D, to a closed position as shown in FIG. 6C.

In one embodiment, tip 27 can be comprised of two or more pieces, each tip piece attached by one of a plurality of hinges 271. In one embodiment, tip 27 can be a flexible absorbent material as shown in FIG. 6A. In such embodiment, hinge 271 can merely refer to the portion of tip near tube where the tip will bend as viewing scope 26 passes through.

FIG. 7 illustrates cannula shaft 29 already introduced into and through the patient's skin 23. Viewing scope 26 has been slidably introduced into lumen 14 via proximal access port 18 of cannula and scope cleaning apparatus 2, the viewing scope 26 abutting the proximal side of lens-cleaning portion 8, which can be comprised of absorbent pads with or without a cleaning solution already preloaded into cleaning portion 8. Both viewing scope 26 and cannula and scope cleaning apparatus 2 thereon are introduced into cannula 28 and advanced toward the patient. The least one coupling mechanism extension 38, having a cannula-engaging portion 36, enters a corresponding opening in cannula collar 32. The combination viewing scope 26 and cannula and scope cleaning apparatus 2 are advanced past the distal tip of cannula 29, the scope 26 still being retained within cannula and scope cleaning apparatus 2. Advantageously, in some embodiments, tip 27 may comprise a transparent or translucent material in order to facilitate light transmission to viewing scope 26, light being provided by an illumination source previously introduced into the patient. Passageway in lens-cleaning portion 8 can be of sufficient width to allow visibility of the area of the distal portion of the cannula and scope cleaning apparatus 2. Thus, an operator can discern by means of viewing scope 26 when the viewing scope 26 (within the cannula and scope cleaning apparatus 2) has passed the distal tip of cannula shaft 29, as shown in FIG. 7. As one aspect, by providing cannula and scope cleaning apparatus 2 having an overall length that is longer than cannula length (i.e. being able to push cannula and scope cleaning apparatus 2 past distal tip of cannula shaft 29), unwanted debris (bodily fluid/debris) within cannula is advantageously cleared out well past from within cannula 28 and past distal tip of cannula shaft 29 upon insertion of cannula and scope cleaning apparatus 2 therein.

FIG. 8 illustrates cannula and scope cleaning apparatus 2 in a withdrawn position, for example, once the viewing scope 26 has been positioned in a desired location. In this figure, cannula and scope cleaning apparatus 2 are retracted or withdrawn in a proximal direction by operator, with viewing scope 26 distal tip remaining in the desired position as shown. Upon retraction of cannula and scope cleaning apparatus 2, the cannula coupling mechanism 34 secures the cannula and scope cleaning apparatus 2 relative to cannula 28, for example, by cannula engaging portions 36 of coupling mechanism extensions 38 engaging recesses 33 in cannula collar 32, as shown. With cannula and scope cleaning apparatus 2 so engaged in position, the operator can view the surgical site or surgical procedure, without need to further manipulate cannula and scope cleaning apparatus 2.

During the surgical procedure, whenever the distal end or lens 24 of viewing scope 26 becomes contaminated with debris, fog, or other obscuring media, lens 24 of scope 26 can be cleaned by withdrawing viewing scope 26 in a direction away from the surgical site, toward lens-cleaning portion 8, so that lens 24 can re-enter into the interior of lens-cleaning portion 8 such that the passageway of lens-cleaning portion 8 contacts and engages the lens 24. The lens 24 can therefore be cleaned or scrubbed, for example, by reciprocating the viewing scope 26 in a forward and reverse motion and/or rotating the lens 24 within the lens-cleaning portion 8. Such cleaning/clearing maneuvers can be utilized in accordance with any configuration of cannula and scope cleaning apparatus 2, as taught by the instant disclosure.

Figure 9:
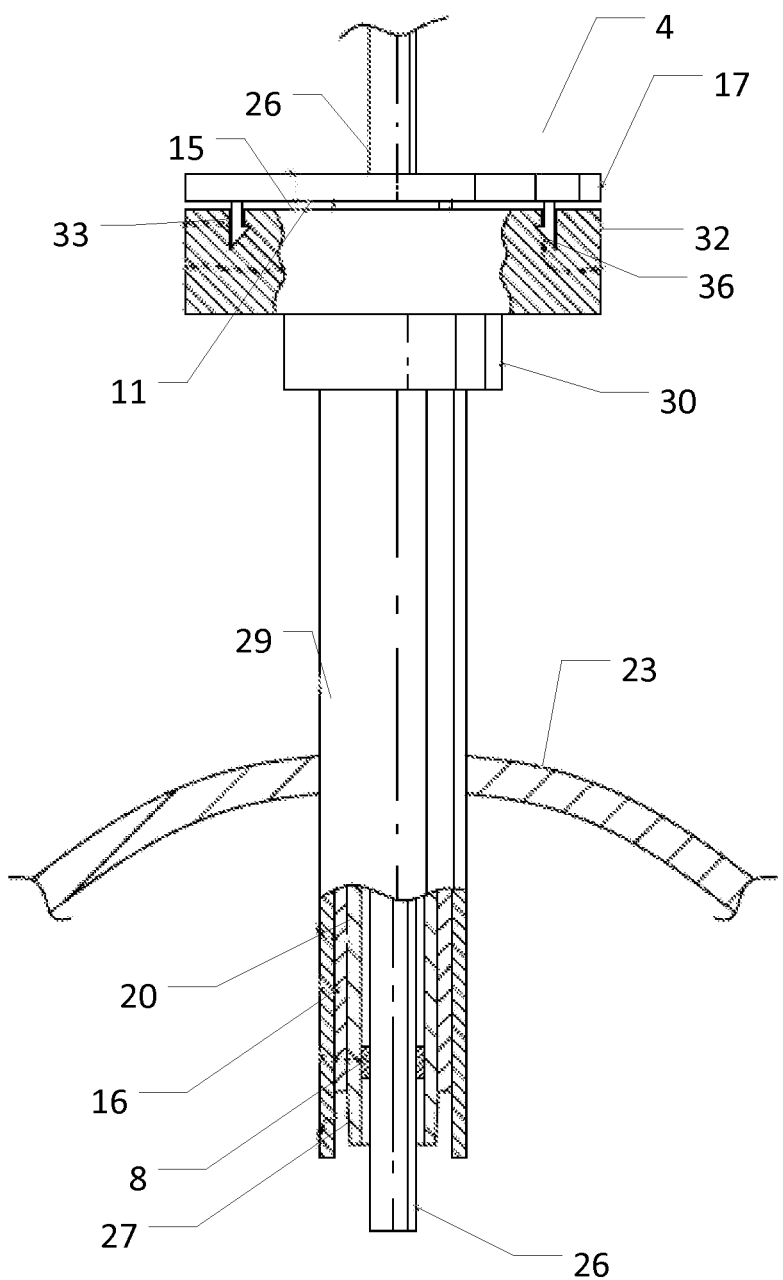
FIG. 9 illustrates another embodiment according to the present disclosure, where an exemplary cannula and trocar cleaning apparatus is of an overall length such that it cannot extend past the distal end of a cannula, and is secured to the collar of a cannula.

FIG. 9 illustrates an embodiment wherein cannula and scope cleaning apparatus 2 is of a length such that it does not extend past distal tip of cannula shaft 29 upon insertion into cannula 28. Thus no retraction is necessary to maintain the distal portion of cannula and -scope cleaning apparatus 2 within cannula shaft 29. Cannula and scope cleaning apparatus 2 is inserted into cannula 28 until collar 4 engages cannula collar 32 via a coupling mechanism. In the embodiment depicted in FIG. 9, cannula engaging portions 36 engaging recesses 33 in cannula collar 32 as shown. The coupling mechanism can be provided in any configuration that securely engages cannula and scope cleaning apparatus 2 and cannula 28 to one another, such as a twist lock, at least one lug fitting into a corresponding recess and the like. As depicted, the viewing scope 26 passes and opens tip 27 within cannula shaft 29, and thus tip 27 does not pass distal portion of cannula shaft 29.

A cannula-engaging portion of cannula and scope cleaning apparatus 2 can be provided having such a configuration such that it engages the recesses and locking mechanism typically already present in cannulas that are provided in conjunction with a lockable/removable trocar. In this way, cannula and scope cleaning apparatus 2, having engaging portions that mimic those well-known locking mechanisms already in use (engaging and locking trocars to cannulas), can be utilized with trocar/cannula combos presently available on the market.

Figure 10A:
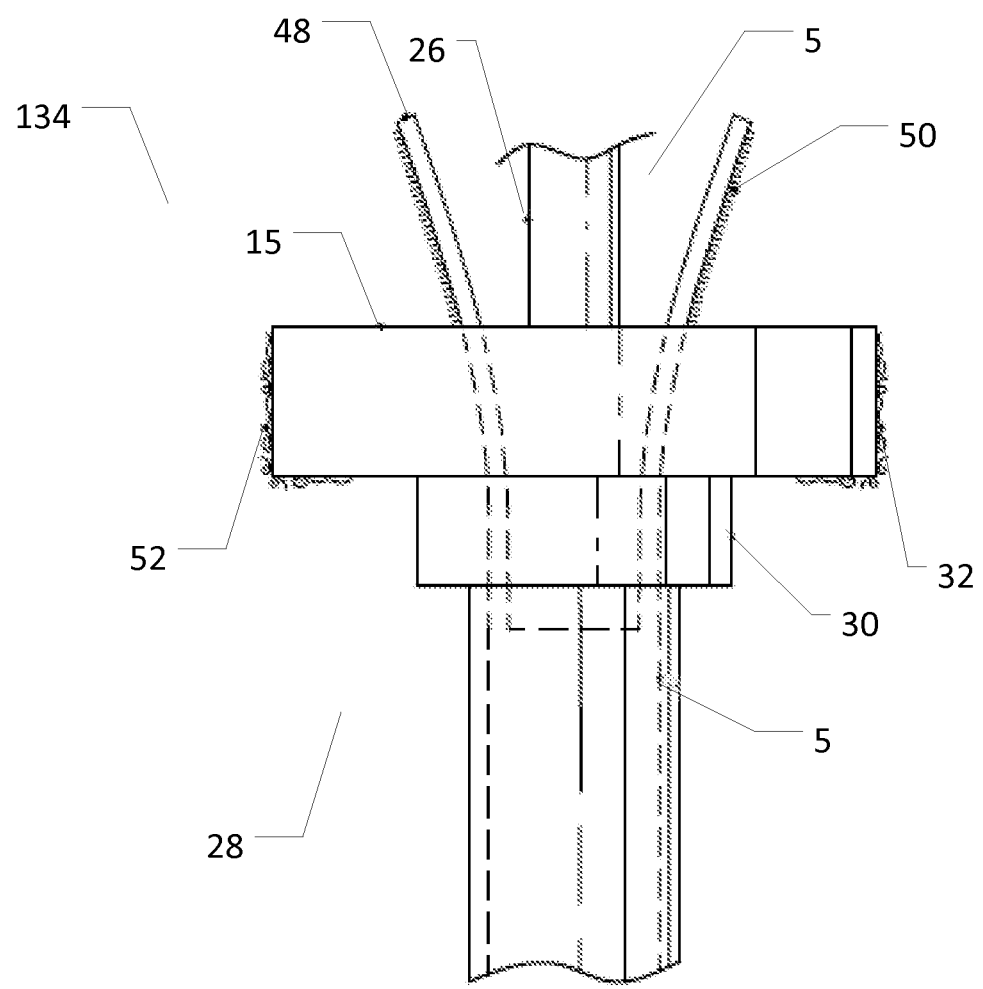
FIG. 10A illustrates another embodiment of an exemplary coupling mechanism, before coupling, to a cannula.
Figure 10B:
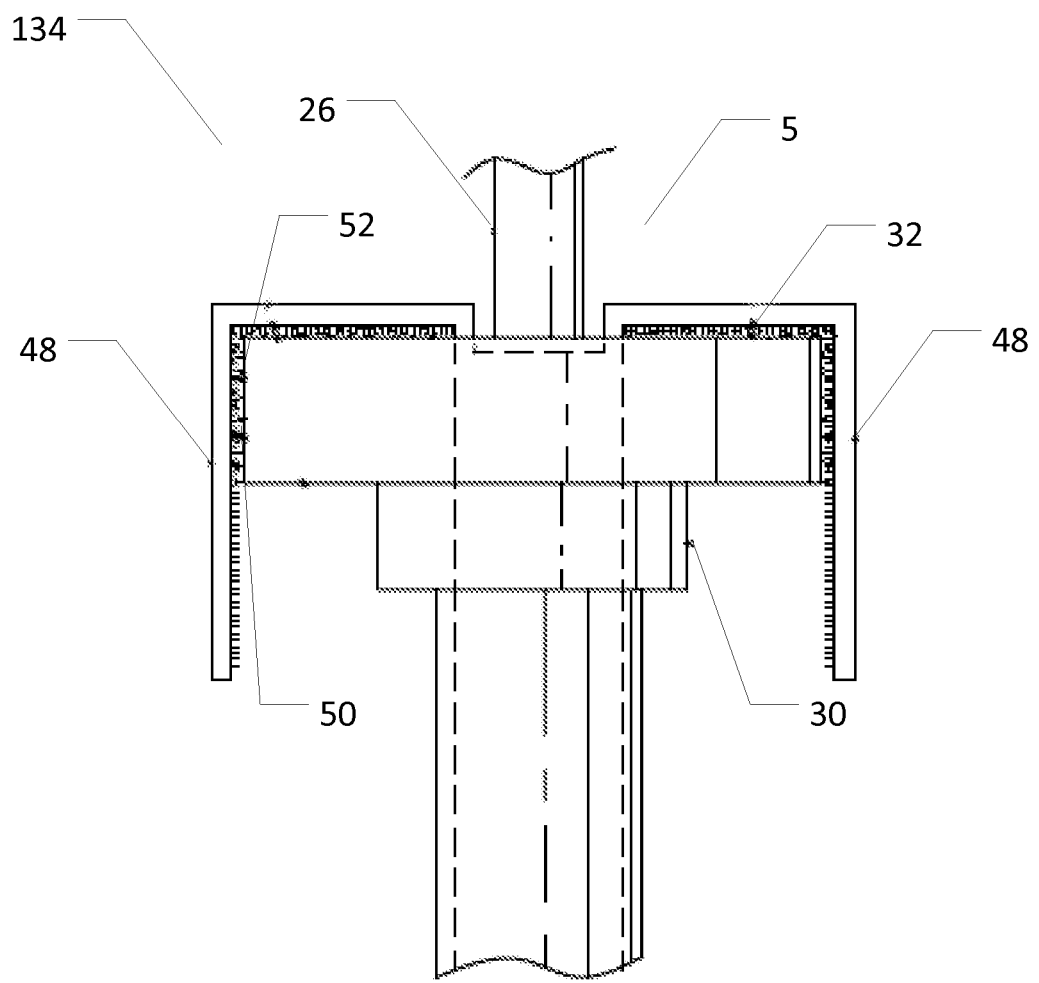
FIG. 10B illustrates another embodiment of an exemplary coupling mechanism, after coupling, to a cannula.

FIGS. 10A and 10B illustrate another embodiment cannula coupling mechanism 134 which can be an alternative to cannula-coupling mechanism 34 shown in FIGS. 7 and 8. Cannula-coupling mechanism 134 has a similar function to cannula-coupling mechanism 34, such that upon withdrawing cannula and scope cleaning apparatus 2 within cannula 28, cannula-coupling mechanism 134 fixes cannula and scope cleaning apparatus 2 in place relative to cannula 28. In the embodiment shown, tube 5 of cannula and scope cleaning apparatus 2 includes, at its proximal end, flexible tabs 48. Flexible tabs 48 are structured to be securable, or removably securable, to cannula 28 when cannula and scope cleaning apparatus 2 is in the withdrawn position, as shown in FIG. 10B. For example, tabs 48 may include hook and loop fastening surface 50 capable of engaging cooperative hook and loop fastening surface 52 of cannula collar 32. Other mechanisms for securing tabs 48 to cannula 28 are contemplated and are considered to be within the scope of the present invention. For example, pegs on cannula collar 32 and corresponding cooperative apertures on tabs 48, adhesives, magnetic elements and/or other suitable securing means can be provided on tabs 48 and cannula collar 32 to provide secured engagement therebetween.

Figure 11B:
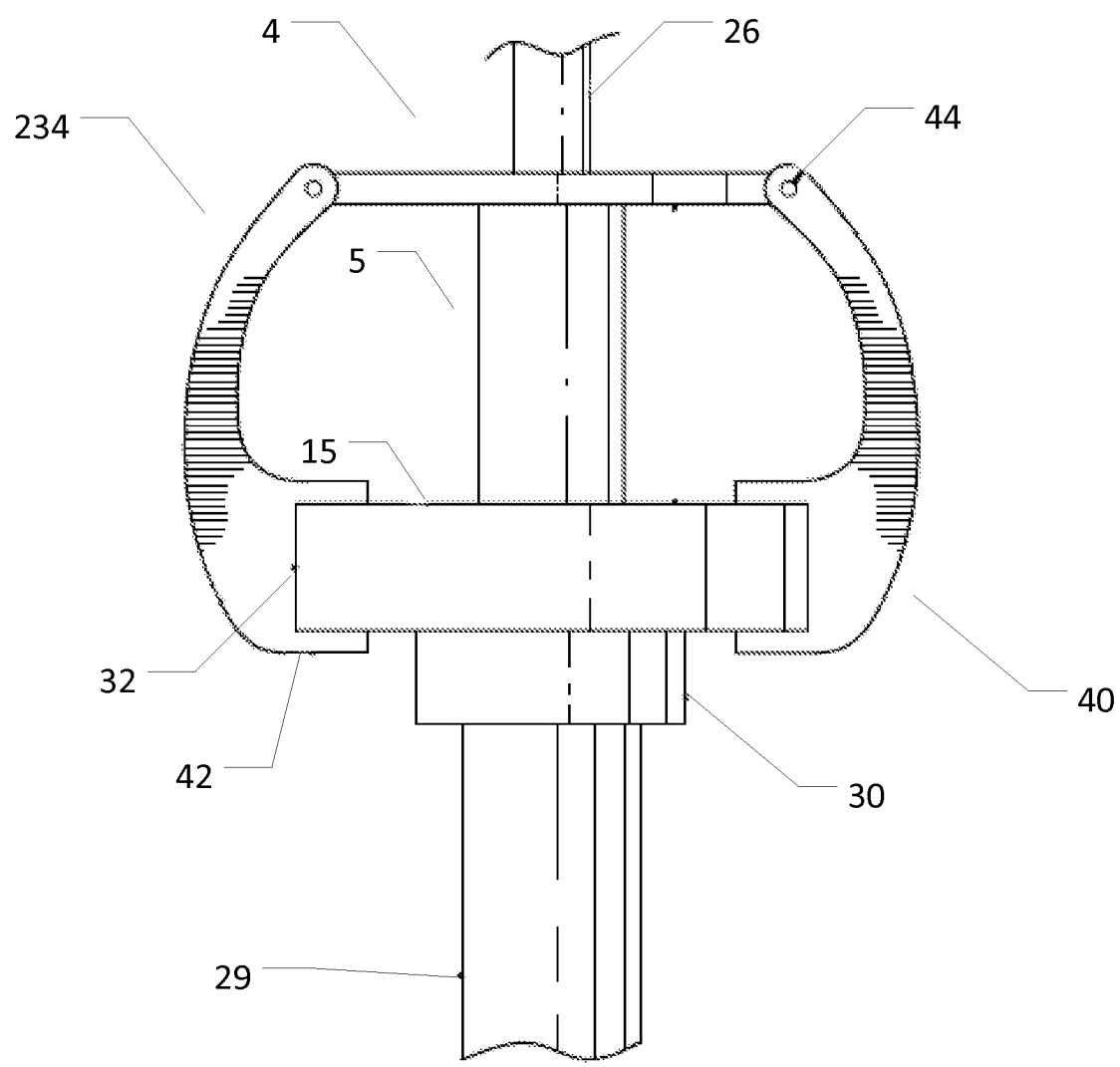
FIG. 11B illustrates yet another embodiment of an exemplary coupling mechanism, after coupling, to a cannula.

FIGS. 11A and 11B illustrate another alternative cannula coupling mechanism 234, before and after securing cannula and scope cleaning apparatus 2, respectively, to cannula 28. In one embodiment, cannula-coupling mechanism 234 comprises one or more pivoting elements 40 structured to engage cannula collar 32. The example in FIG. 11B comprises two pivoting elements. In the embodiment shown, each pivoting element 40 includes a hinge or pivot 44 at collar 4, and a distal engaging structure, for example, in the form of a clamp 42 or the like. Turning now specifically to FIG. 12B, when the cannula and scope cleaning apparatus 2 is in the withdrawn position and clamp 42 is engaged to cannula collar 32, pivoting elements 40 may define a fixed distance R.sub.d, that is, a fixed retraction distance. As an example, R.sub.d can be about 1.5 cm or less, preferably about 1 cm or less.

The cannula and scope cleaning apparatus disclosed herein can also be designed to be disposed of after a single use, or it can be designed to be used multiple times. In either case, however, the cannula and scope cleaning apparatus can be reconditioned for reuse after at least one use. Reconditioning can include any combination of the steps of disassembly of the cannula and scope cleaning apparatus, followed by cleaning or replacement of particular pieces and subsequent reassembly. In particular, the cannula and scope cleaning apparatus can be disassembled, and any number of the particular pieces or parts of the cannula and scope cleaning apparatus can be selectively replaced or removed in any combination. Those skilled in the art will appreciate that reconditioning of a cannula and scope cleaning apparatus can utilize a variety of techniques for disassembly, cleaning/replacement, and reassembly. Use of such techniques, and the resulting reconditioned cannula and scope cleaning apparatus, are all within the scope of the present application.

Although the present disclosure has been described and illustrated with a certain degree of particularity, it is understood that the present disclosure has been made only by way of example and that numerous changes in the combination and arrangement of parts can be resorted to by those skilled in the art without departing from the spirit and scope of the invention. While there have been described above the principles of the present disclosure in conjunction with a cannula and scope cleaning apparatus and for its associated use, it is to be clearly understood that the foregoing description is made only by way of example and not as a limitation to the scope of the disclosure. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features presented and taught herein in any patent application derived therefrom.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. An apparatus for use with a cannula and a viewing scope, the apparatus comprising:
a tube having an elongate rigid structure,
wherein the tube is sized to be inserted in a cannula; and
wherein the tube comprises an inner surface that defines a lumen and is configured to receive therein a viewing scope; and
a tip connected by a hinge to the tube, wherein the tip, hinge and a distal portion of the tube are continuous as a single piece.

2. The apparatus of claim 1, wherein the tip consists of only one tip and the hinge consists of only one hinge.

3. The apparatus of claim 1, wherein the hinge includes a flexible base that extends into a distal portion of the tube.

4. The apparatus of claim 2, wherein the hinge includes a flexible base that extends into a distal portion of the tube.

5. The apparatus of claim 1, wherein an outer portion of the tip is coupled to an absorbent pad.

6. The apparatus of claim 1, wherein an inner portion of the tip is coupled to an absorbent pad.

7. The apparatus of claim 1, wherein an outer and inner portion of the tip are each coupled to an absorbent pad.

8. The apparatus of claim 1, wherein the lumen includes a scaffold that extends along at least a portion of the lumen.

9. The apparatus of claim 1, wherein the lumen includes a scaffold that extends along the entire lumen.

10. The apparatus of claim 8, wherein the scaffold is radially compressible.

11. The apparatus of claim 9, wherein the scaffold is radially compressible.

12. The apparatus of claim 1, wherein the tube includes an outer surface having at least a portion of which is absorbent.

13. The apparatus of claim 1, wherein the tube includes an outer surface having at least a portion of which is compressible.

14. The apparatus of claim 1, further comprising a collar portion at a proximal portion of the tube, where the collar portion abuts a proximal portion of the cannula upon insertion of the apparatus into the cannula.

15. An apparatus for use with a cannula and a viewing scope, the apparatus comprising:
a tube having an elongate rigid structure,
wherein the tube is configured to be slidably received by a cannula; and
wherein the tube comprises an inner surface that defines a lumen and is configured to slidably receive a viewing scope; and
a tip connected by a hinge to the tube, wherein the tube, hinge, and a distal portion of the tube are continuous as a single piece, and
wherein at least one portion of the tip is coupled to an absorbent pad.

16. The apparatus of claim 15, wherein the lumen includes a scaffold that extends along at least a portion of the lumen.

17. The apparatus of claim 15, wherein the tube includes an outer surface having at least a portion of which is absorbent.

18. The apparatus of claim 15, wherein the tube includes an outer surface having at least a portion of which is compressible.

* * * * *